United States Patent
Welting et al.

(10) Patent No.: US 10,639,352 B2
(45) Date of Patent: May 5, 2020

(54) METHOD FOR THE TREATMENT OR PREVENTION OF OSTEOARTHRITIS

(71) Applicant: Chondropeptix B.V., Maastricht (NL)

(72) Inventors: Tim Johannes Maria Welting, Klimmen (NL); Marjolein Maria Johanna Caron, Maastricht (NL)

(73) Assignee: Chondropeptix B.V., Maastricht (NL)

( * ) Notice: Subject to any disclaimer, the term of this patent is extended or adjusted under 35 U.S.C. 154(b) by 0 days.

(21) Appl. No.: 16/092,680

(22) PCT Filed: Mar. 31, 2017

(86) PCT No.: PCT/EP2017/057720
§ 371 (c)(1),
(2) Date: Oct. 10, 2018

(87) PCT Pub. No.: WO2017/178253
PCT Pub. Date: Oct. 19, 2017

(65) Prior Publication Data
US 2019/0125838 A1    May 2, 2019

(30) Foreign Application Priority Data

Apr. 13, 2016   (EP) .................................... 16165106

(51) Int. Cl.
*A61K 38/10* (2006.01)
*A61K 38/16* (2006.01)
*A61K 38/18* (2006.01)
*A61P 19/02* (2006.01)

(52) U.S. Cl.
CPC .......... *A61K 38/1875* (2013.01); *A61K 38/10* (2013.01); *A61K 38/16* (2013.01); *A61P 19/02* (2018.01)

(58) Field of Classification Search
None
See application file for complete search history.

(56) References Cited

U.S. PATENT DOCUMENTS 7,015,311 B1 *  3/2006  Johnson ............... C07K 14/475
424/145.1

FOREIGN PATENT DOCUMENTS

WO   WO 2006/009836    *  1/2006
WO   WO2009154330 A1   12/2009
WO   WO2011163398 A2   12/2011

OTHER PUBLICATIONS

Caron, et al. "Hypertrophic Differentiation During Chondrogenic Differentiation of Progenitor Cells Is Stimulated by Bmp-2 but Suppressed by Bmp-7." Osteoarthritis and Cartilage. 21.4 (2013): 604-613. http://dx.doi.org/10.1016/j.joca.2013.01.009-XP055293553.
Chen, et al. "Increased Osteoblast Functions in the Presence of Bmp-7 Short Peptides for Nanostructured Biomaterial Applications." Journal of Biomedical Materials Research—Part A. 91.1 (2009): 296-304. http://dx.doi.org/10.1002/jbm.a.32246-XP055293547.
Hayashi, et al. "Weekly Intra-Articular Injections of Bone Morphogenetic Protein-7 Inhibits Osteoarthritis Progression." Arthritis Research and Therapy. 10.5 (2008). http://dx.doi.org/10.1186/ar2521 XP021046821.
Hunter et al. "Phase 1 Safety and Tolerability Study of Bmp-7 in Symptomatic Knee Osteoarthritis." Bmc Musculoskeletal Disorders. 11.1 (2010): 1-8. XP021076295 http://dx.doi.org/10.1186/1471-2474-11-232.
PCT International Search Report and Written Opinion, Application No. PCT/EP2017/057720, dated May 17, 2017.
Saito, et al., "Accelerated Bone Repair with the Use of a Synthetic Bmp-2-Derived Peptide and Bone-Marrow Stromal Cells." Journal of Biomedical Materials Research Part a. (2005): 77-82. http://dx.doi.org/10.1002/jbm.a.30208-XP055177958.

* cited by examiner

*Primary Examiner* — Sergio Coffa
(74) *Attorney, Agent, or Firm* — Patent Law Works LLP

(57)   ABSTRACT

The present invention is in the field of medicine and provides means and methods for the treatment, prevention or amelioration of osteoarthritis. More in particular, it provides a peptide for use in the treatment, amelioration or prevention of osteoarthritis, wherein the peptide consists of an amino acid sequence according to SEQ ID NO: 18 or an analogue thereof, wherein the analogue is a peptide consisting of an amino acid sequence according to formula 1 (SEQ ID NO: 29), or a fragment thereof wherein the fragment consists of at least 10 consecutive amino acids of SEQ ID NO: 18 or an amino acid sequence according to formula 1.

Figure 1:
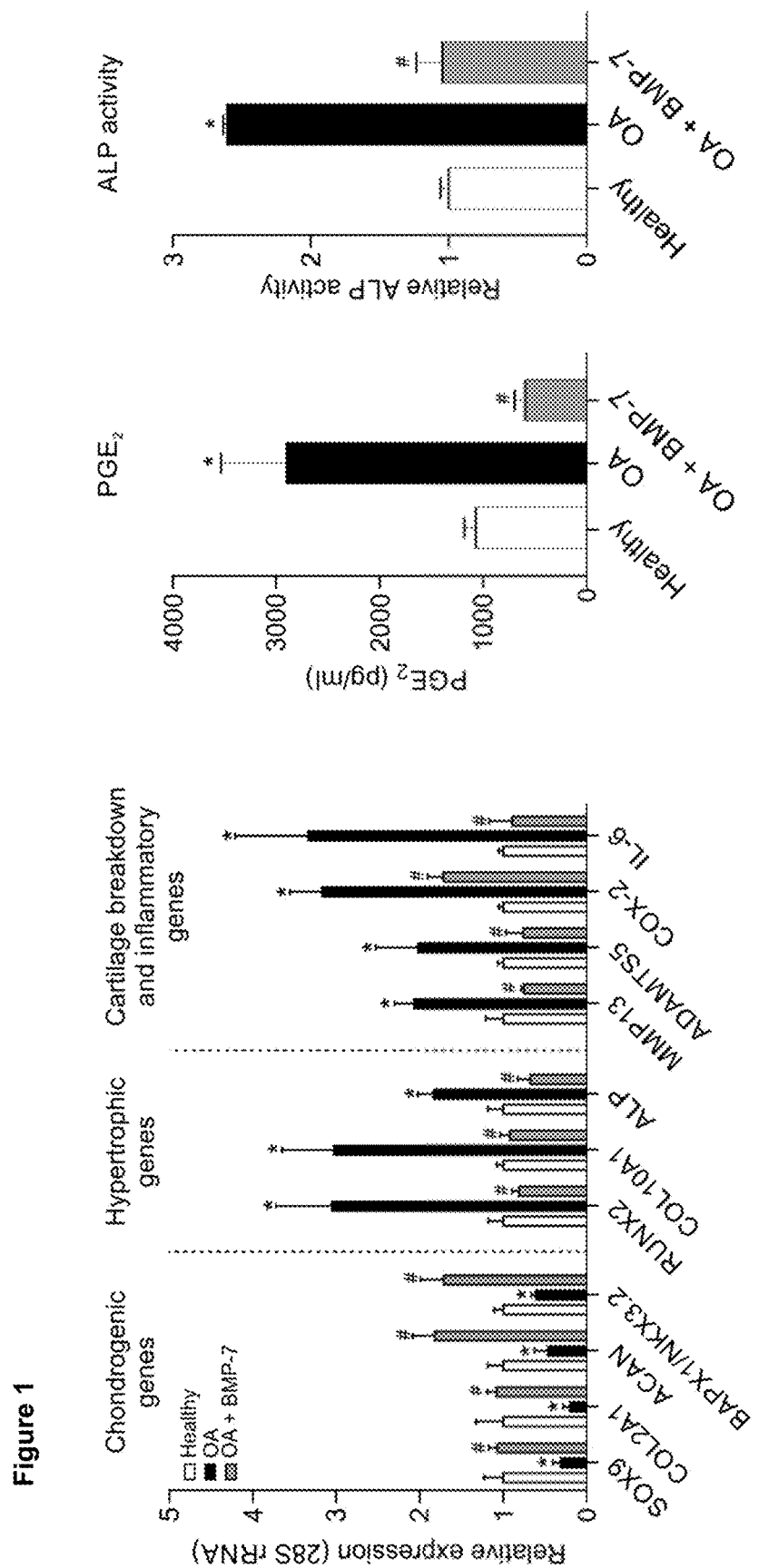
Figure 2:
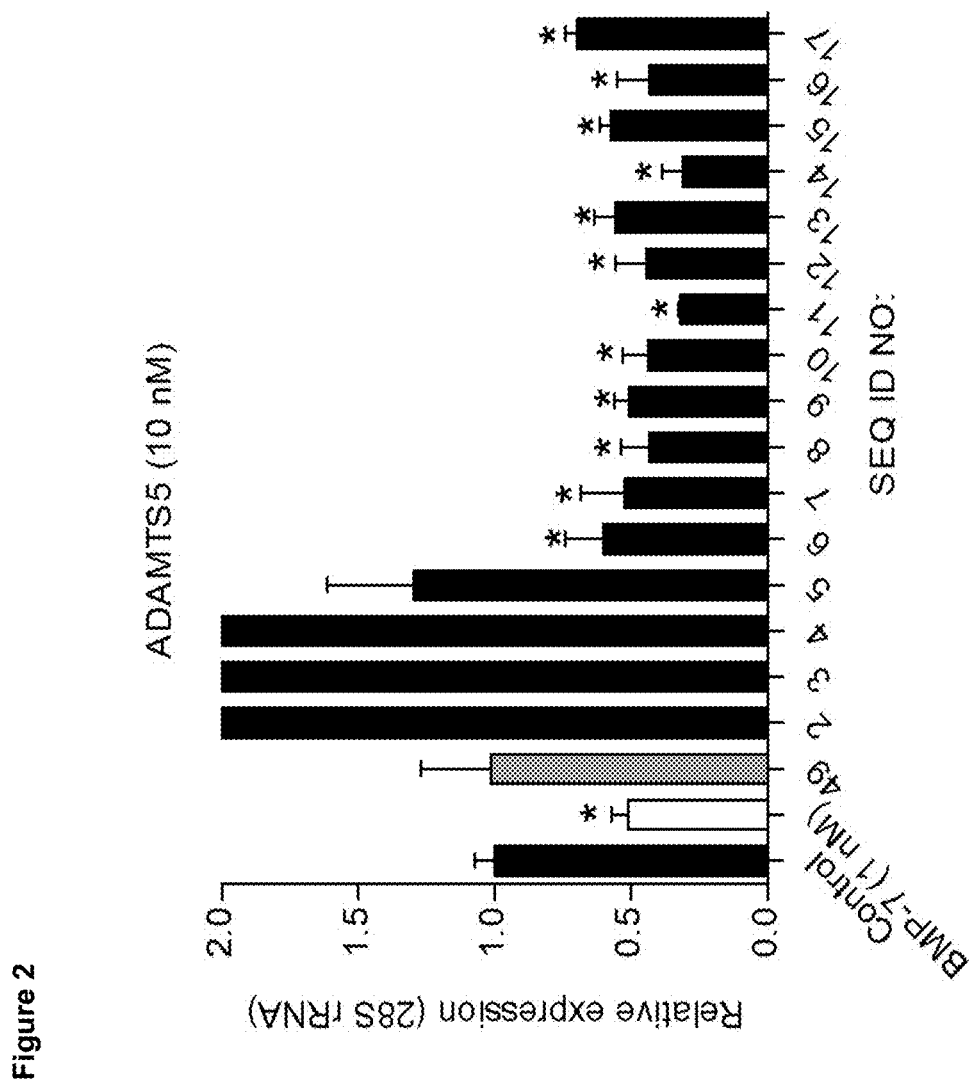
Figure 3:
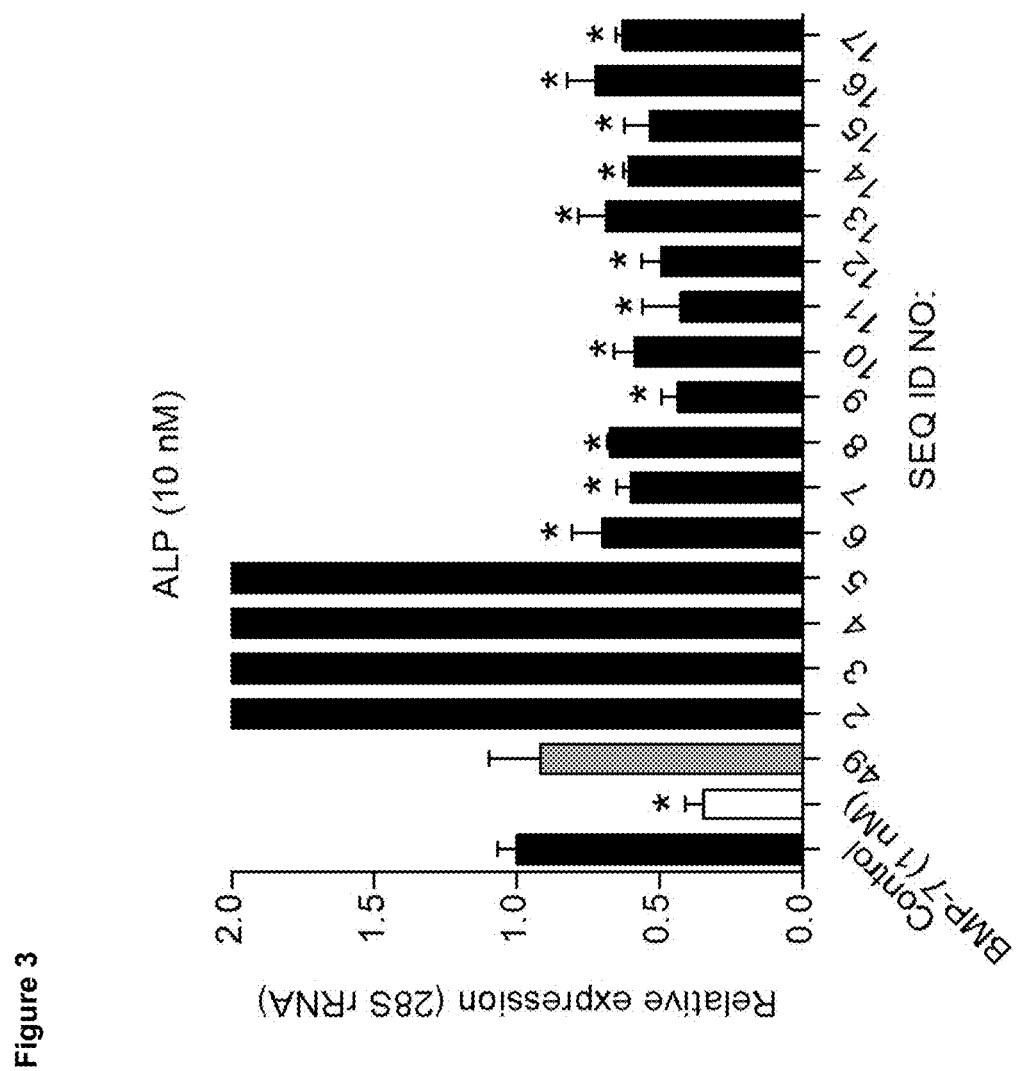
Figure 4:
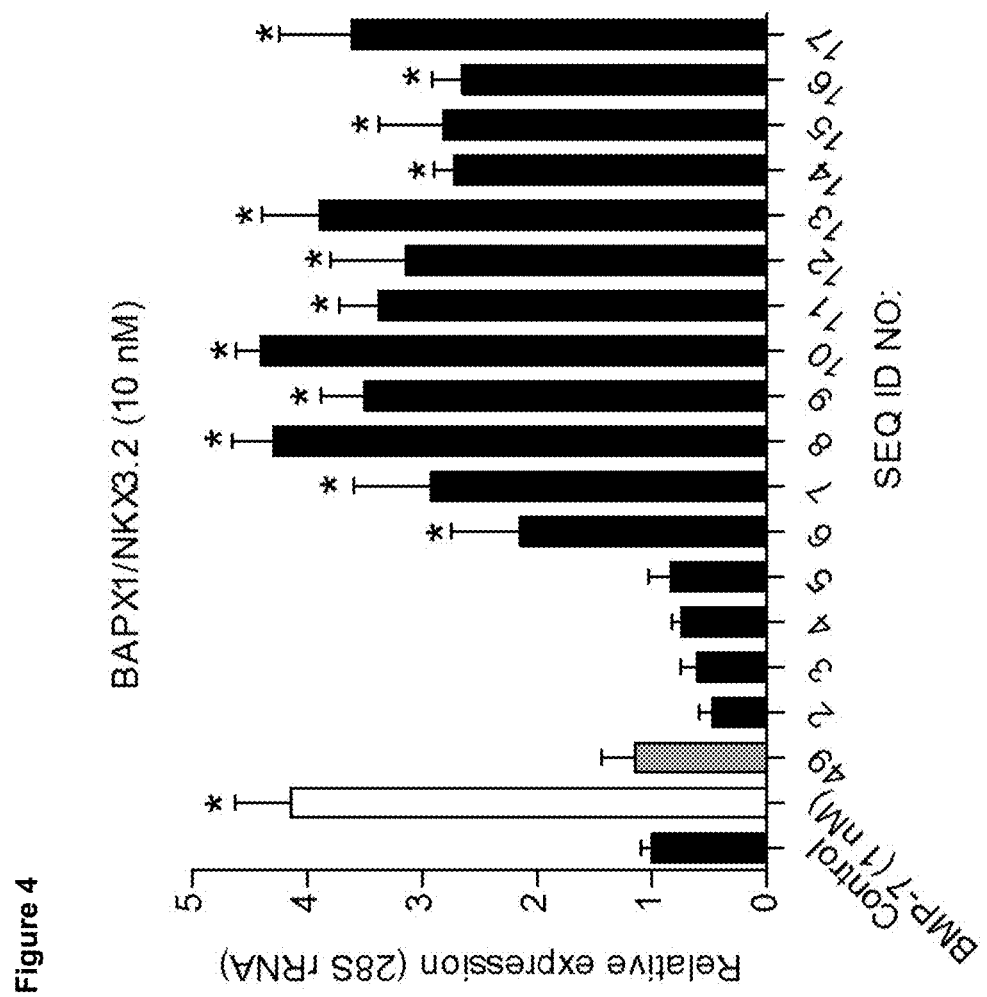
Figure 5:
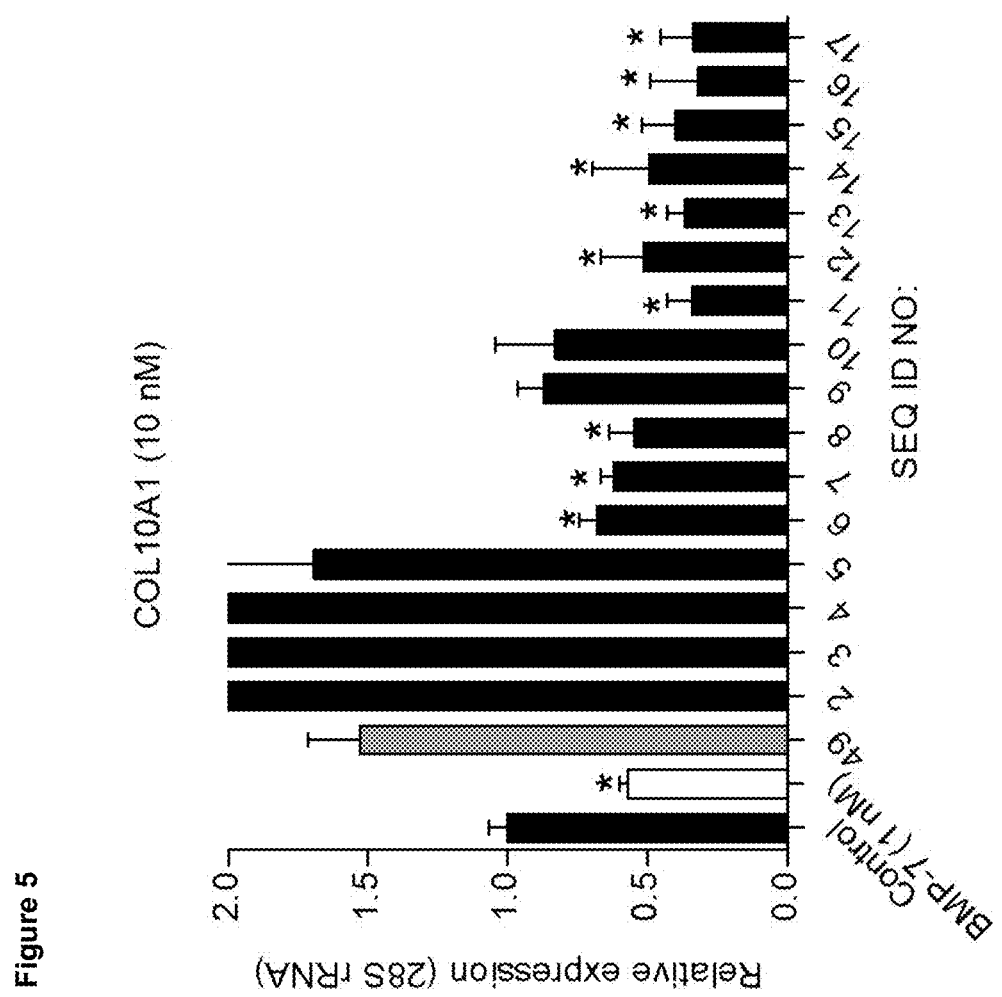
Figure 6:
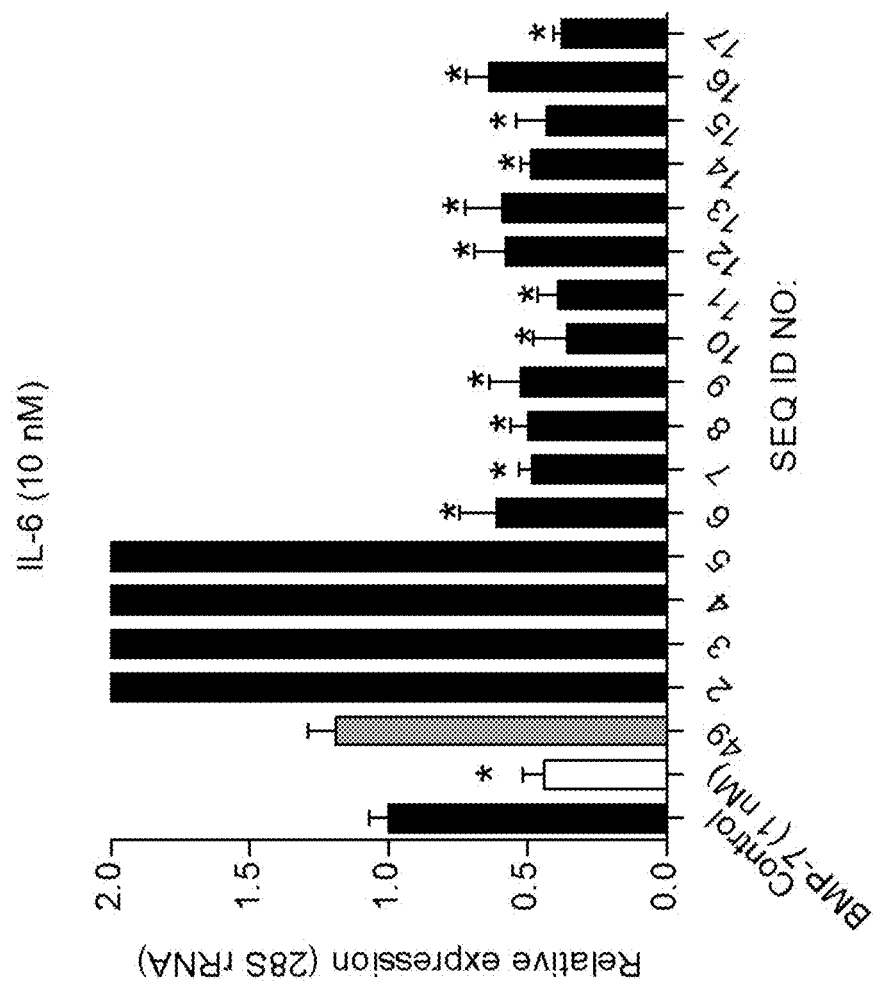
Figure 7:
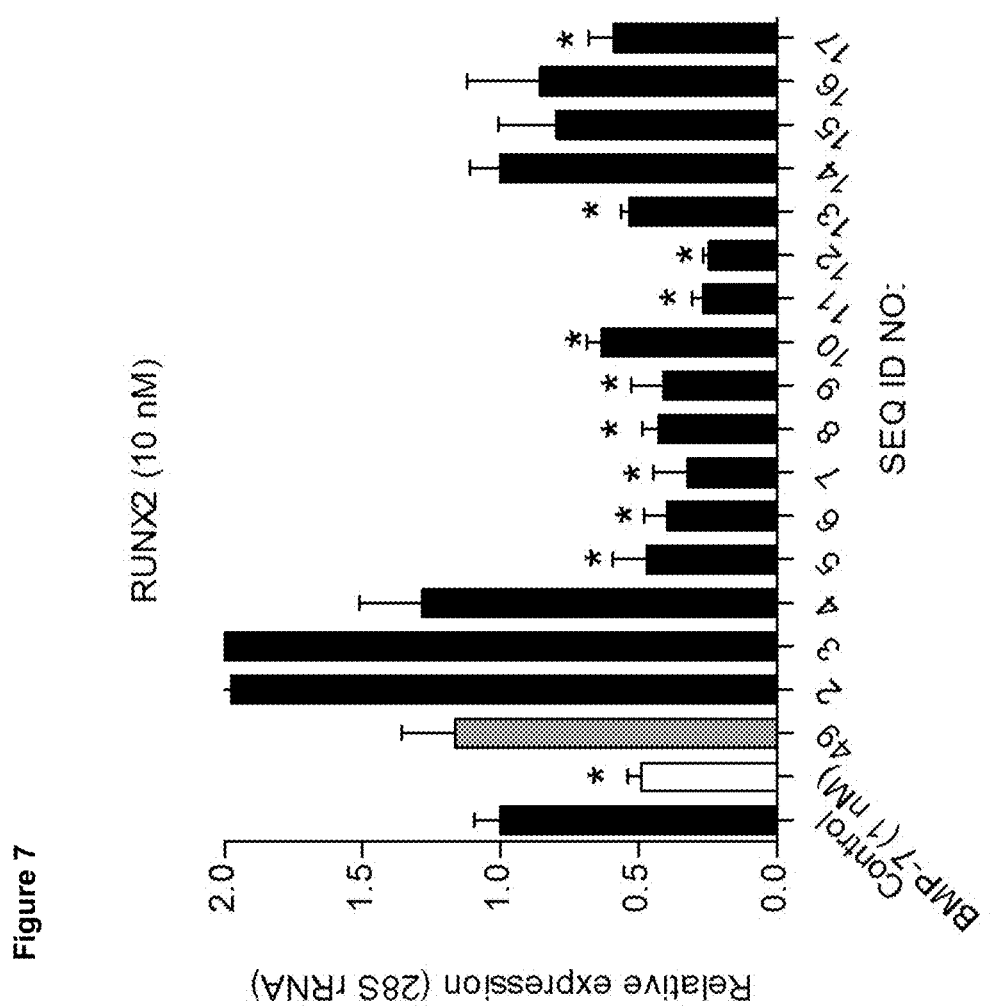

10 Claims, 9 Drawing Sheets
Specification includes a Sequence Listing.

SEQUENCE LISTING

<160> NUMBER OF SEQ ID NOS: 64

<210> SEQ ID NO 1
<211> LENGTH: 47
<212> TYPE: PRT
<213> ORGANISM: Homo sapiens

<400> SEQUENCE: 1

Phe Ile Asn Pro Glu Thr Val Pro Lys Pro Ser Ser Ala Pro Thr Gln
1               5                   10                  15

Leu Asn Ala Ile Ser Val Leu Tyr Phe Asp Asp Ser Ser Asn Val Ile
            20                  25                  30

Leu Lys Lys Tyr Arg Asn Met Val Val Arg Ala Ser Gly Ser His
        35                  40                  45

<210> SEQ ID NO 2
<211> LENGTH: 20
<212> TYPE: PRT
<213> ORGANISM: Homo sapiens

<400> SEQUENCE: 2

Phe Ile Asn Pro Glu Thr Val Pro Lys Pro Ser Ser Ala Pro Thr Gln
1               5                   10                  15

Leu Asn Ala Ile
            20

<210> SEQ ID NO 3
<211> LENGTH: 20
<212> TYPE: PRT
<213> ORGANISM: Homo sapiens

<400> SEQUENCE: 3

Asn Pro Glu Thr Val Pro Lys Pro Ser Ser Ala Pro Thr Gln Leu Asn
1               5                   10                  15

Ala Ile Ser Val
            20

<210> SEQ ID NO 4
<211> LENGTH: 20
<212> TYPE: PRT
<213> ORGANISM: Homo sapiens

<400> SEQUENCE: 4

Glu Thr Val Pro Lys Pro Ser Ser Ala Pro Thr Gln Leu Asn Ala Ile
1               5                   10                  15

Ser Val Leu Tyr
            20

<210> SEQ ID NO 5
<211> LENGTH: 20
<212> TYPE: PRT
<213> ORGANISM: Homo sapiens

<400> SEQUENCE: 5

Val Pro Lys Pro Ser Ser Ala Pro Thr Gln Leu Asn Ala Ile Ser Val
1               5                   10                  15

Leu Tyr Phe Asp
            20

<210> SEQ ID NO 6
<211> LENGTH: 20
<212> TYPE: PRT
<213> ORGANISM: Homo sapiens

<400> SEQUENCE: 6

Pro Lys Pro Ser Ser Ala Pro Thr Gln Leu Asn Ala Ile Ser Val Leu
1               5                   10                  15

Tyr Phe Asp Asp
            20

<210> SEQ ID NO 7
<211> LENGTH: 20
<212> TYPE: PRT
<213> ORGANISM: Homo sapiens

<400> SEQUENCE: 7

Lys Pro Ser Ser Ala Pro Thr Gln Leu Asn Ala Ile Ser Val Leu Tyr

```
1               5                   10                  15

Phe Asp Asp Ser
            20

<210> SEQ ID NO 8
<211> LENGTH: 20
<212> TYPE: PRT
<213> ORGANISM: Homo sapiens

<400> SEQUENCE: 8

Ser Ser Ala Pro Thr Gln Leu Asn Ala Ile Ser Val Leu Tyr Phe Asp
1               5                   10                  15

Asp Ser Ser Asn
            20

<210> SEQ ID NO 9
<211> LENGTH: 20
<212> TYPE: PRT
<213> ORGANISM: Homo sapiens

<400> SEQUENCE: 9

Ala Pro Thr Gln Leu Asn Ala Ile Ser Val Leu Tyr Phe Asp Asp Ser
1               5                   10                  15

Ser Asn Val Ile
            20

<210> SEQ ID NO 10
<211> LENGTH: 20
<212> TYPE: PRT
<213> ORGANISM: Homo sapiens

<400> SEQUENCE: 10

Thr Gln Leu Asn Ala Ile Ser Val Leu Tyr Phe Asp Asp Ser Ser Asn
1               5                   10                  15

Val Ile Leu Lys
            20

<210> SEQ ID NO 11
<211> LENGTH: 20
<212> TYPE: PRT
<213> ORGANISM: Homo sapiens

<400> SEQUENCE: 11

Leu Asn Ala Ile Ser Val Leu Tyr Phe Asp Asp Ser Ser Asn Val Ile
1               5                   10                  15

Leu Lys Lys Tyr
            20

<210> SEQ ID NO 12
<211> LENGTH: 20
<212> TYPE: PRT
<213> ORGANISM: Homo sapiens

<400> SEQUENCE: 12

Ala Ile Ser Val Leu Tyr Phe Asp Asp Ser Ser Asn Val Ile Leu Lys
1               5                   10                  15

Lys Tyr Arg Asn
            20

<210> SEQ ID NO 13
<211> LENGTH: 20
<212> TYPE: PRT
```

<213> ORGANISM: Homo sapiens

<400> SEQUENCE: 13

Ser Val Leu Tyr Phe Asp Asp Ser Ser Asn Val Ile Leu Lys Lys Tyr
1               5                   10                  15

Arg Asn Met Val
            20

<210> SEQ ID NO 14
<211> LENGTH: 20
<212> TYPE: PRT
<213> ORGANISM: Homo sapiens

<400> SEQUENCE: 14

Leu Tyr Phe Asp Asp Ser Ser Asn Val Ile Leu Lys Lys Tyr Arg Asn
1               5                   10                  15

Met Val Val Arg
            20

<210> SEQ ID NO 15
<211> LENGTH: 20
<212> TYPE: PRT
<213> ORGANISM: Homo sapiens

<400> SEQUENCE: 15

Phe Asp Asp Ser Ser Asn Val Ile Leu Lys Lys Tyr Arg Asn Met Val
1               5                   10                  15

Val Arg Ala Ser
            20

<210> SEQ ID NO 16
<211> LENGTH: 20
<212> TYPE: PRT
<213> ORGANISM: Homo sapiens

<400> SEQUENCE: 16

Asp Ser Ser Asn Val Ile Leu Lys Lys Tyr Arg Asn Met Val Val Arg
1               5                   10                  15

Ala Ser Gly Ser
            20

<210> SEQ ID NO 17
<211> LENGTH: 20
<212> TYPE: PRT
<213> ORGANISM: Homo sapiens

<400> SEQUENCE: 17

Ser Ser Asn Val Ile Leu Lys Lys Tyr Arg Asn Met Val Val Arg Ala
1               5                   10                  15

Ser Gly Ser His
            20

<210> SEQ ID NO 18
<211> LENGTH: 40
<212> TYPE: PRT
<213> ORGANISM: Homo sapiens

<400> SEQUENCE: 18

Pro Lys Pro Ser Ser Ala Pro Thr Gln Leu Asn Ala Ile Ser Val Leu
1               5                   10                  15

Tyr Phe Asp Asp Ser Ser Asn Val Ile Leu Lys Lys Tyr Arg Asn Met
            20                  25                  30

Val Val Arg Ala Ser Gly Ser His
            35                  40

<210> SEQ ID NO 19
<211> LENGTH: 20
<212> TYPE: PRT
<213> ORGANISM: Homo sapiens

<400> SEQUENCE: 19

Ser Thr Gly Ser Lys Gln Arg Ser Gln Asn Arg Ser Lys Thr Pro Lys
1               5                   10                  15

Asn Gln Glu Ala
            20

<210> SEQ ID NO 20
<211> LENGTH: 30
<212> TYPE: PRT
<213> ORGANISM: Homo sapiens

<400> SEQUENCE: 20

Lys Thr Pro Lys Asn Gln Glu Ala Leu Arg Met Ala Asn Val Ala Glu
1               5                   10                  15

Asn Ser Ser Ser Ser Ser Asp Gln Arg Gln Ala Cys Lys Lys
            20                  25                  30

<210> SEQ ID NO 21
<211> LENGTH: 20
<212> TYPE: PRT
<213> ORGANISM: Homo sapiens

<400> SEQUENCE: 21

Ser Ser Asp Gln Arg Gln Ala Cys Lys Lys His Glu Leu Tyr Val Ser
1               5                   10                  15

Phe Arg Asp Leu
            20

<210> SEQ ID NO 22
<211> LENGTH: 20
<212> TYPE: PRT
<213> ORGANISM: Homo sapiens

<400> SEQUENCE: 22

Asp Leu Gly Trp Gln Asp Trp Ile Ile Ala Pro Glu Gly Tyr Ala Ala
1               5                   10                  15

Tyr Tyr Cys Glu
            20

<210> SEQ ID NO 23
<211> LENGTH: 20
<212> TYPE: PRT
<213> ORGANISM: Homo sapiens

<400> SEQUENCE: 23

Cys Glu Gly Glu Cys Ala Phe Pro Leu Asn Ser Tyr Met Asn Ala Thr
1               5                   10                  15

Asn His Ala Ile
            20

<210> SEQ ID NO 24
<211> LENGTH: 20
<212> TYPE: PRT
<213> ORGANISM: Homo sapiens

```
<400> SEQUENCE: 24

Ala Ile Val Gln Thr Leu Val His Phe Ile Asn Pro Glu Thr Val Pro
1               5                   10                  15

Lys Pro Cys Cys
            20

<210> SEQ ID NO 25
<211> LENGTH: 20
<212> TYPE: PRT
<213> ORGANISM: Homo sapiens

<400> SEQUENCE: 25

Cys Cys Ala Pro Thr Gln Leu Asn Ala Ile Ser Val Leu Tyr Phe Asp
1               5                   10                  15

Asp Ser Ser Asn
            20

<210> SEQ ID NO 26
<211> LENGTH: 20
<212> TYPE: PRT
<213> ORGANISM: Homo sapiens

<400> SEQUENCE: 26

Ser Ser Asn Val Ile Leu Lys Lys Tyr Arg Asn Met Val Val Arg Ala
1               5                   10                  15

Cys Gly Cys His
            20

<210> SEQ ID NO 27
<211> LENGTH: 139
<212> TYPE: PRT
<213> ORGANISM: Homo sapiens

<400> SEQUENCE: 27

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 28
<211> LENGTH: 139
<212> TYPE: PRT
<213> ORGANISM: Homo sapiens

<400> SEQUENCE: 28
```

```
Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Ser Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Ser Glu Gly Glu Ser Ala Phe Pro Leu Asn Ser Tyr Met Asn
65              70                  75                  80

Ala Thr Asn His Ala Ile Val Gln Thr Leu Val His Phe Ile Asn Pro
                85                  90                  95

Glu Thr Val Pro Lys Pro Ser Ser Ala Pro Thr Gln Leu Asn Ala Ile
                100                 105                 110

Ser Val Leu Tyr Phe Asp Asp Ser Ser Asn Val Ile Leu Lys Lys Tyr
            115                 120                 125

Arg Asn Met Val Val Arg Ala Ser Gly Ser His
    130                 135
```

```
<210> SEQ ID NO 29
<211> LENGTH: 40
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (20)..(31)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 29

Pro Lys Pro Ser Ser Xaa Pro Xaa Xaa Leu Xaa Xaa Ile Xaa Val Xaa
1               5                   10                  15

Xaa Xaa Asp Xaa Xaa Xaa Xaa Xaa Xaa Xaa Xaa Xaa Xaa Xaa Xaa Met
            20                  25                  30

Val Val Xaa Xaa Ser Gly Ser Xaa
            35                  40

<210> SEQ ID NO 30
```

-continued

```
<211> LENGTH: 12
<212> TYPE: PRT
<213> ORGANISM: Homo sapiens

<400> SEQUENCE: 30

Tyr Ser Glu Gly Glu Ser Ala Phe Pro Leu Asn Ser
1               5                   10

<210> SEQ ID NO 31
<211> LENGTH: 12
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 31

Tyr Ser Glu Gly Xaa Ser Xaa Xaa Xaa Leu Xaa Xaa
1               5                   10

<210> SEQ ID NO 32
<211> LENGTH: 28
<212> TYPE: PRT
<213> ORGANISM: Homo sapiens

<400> SEQUENCE: 32

Ala Pro Glu Gly Tyr Ala Ala Tyr Tyr Ser Glu Gly Glu Ser Ala Phe
1               5                   10                  15

Pro Leu Asn Ser Tyr Met Asn Ala Thr Asn His Ala
            20                  25

<210> SEQ ID NO 33
<211> LENGTH: 28
<212> TYPE: PRT
<213> ORGANISM: Homo sapiens
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
```

```
<400> SEQUENCE: 33

Xaa Xaa Xaa Gly Tyr Xaa Ala Xaa Tyr Ser Glu Gly Xaa Ser Xaa Xaa
1               5                   10                  15

Xaa Leu Xaa Xaa Xaa Met Asn Ala Thr Xaa His Ala
            20                  25

<210> SEQ ID NO 34
<211> LENGTH: 20
<212> TYPE: PRT
<213> ORGANISM: Homo sapiens

<400> SEQUENCE: 34

Ala Pro Glu Gly Tyr Ala Ala Tyr Tyr Ser Glu Gly Glu Ser Ala Phe
1               5                   10                  15

Pro Leu Asn Ser
            20

<210> SEQ ID NO 35
<211> LENGTH: 20
<212> TYPE: PRT
<213> ORGANISM: Homo sapiens

<400> SEQUENCE: 35

Pro Glu Gly Tyr Ala Ala Tyr Tyr Ser Glu Gly Glu Ser Ala Phe Pro
1               5                   10                  15

Leu Asn Ser Tyr
            20

<210> SEQ ID NO 36
<211> LENGTH: 20
<212> TYPE: PRT
<213> ORGANISM: Homo sapiens

<400> SEQUENCE: 36

Glu Gly Tyr Ala Ala Tyr Tyr Ser Glu Gly Glu Ser Ala Phe Pro Leu
1               5                   10                  15

Asn Ser Tyr Met
            20

<210> SEQ ID NO 37
<211> LENGTH: 20
<212> TYPE: PRT
<213> ORGANISM: Homo sapiens

<400> SEQUENCE: 37

Gly Tyr Ala Ala Tyr Tyr Ser Glu Gly Glu Ser Ala Phe Pro Leu Asn
1               5                   10                  15

Ser Tyr Met Asn
            20

<210> SEQ ID NO 38
<211> LENGTH: 20
<212> TYPE: PRT
<213> ORGANISM: Homo sapiens

<400> SEQUENCE: 38

Tyr Ala Ala Tyr Tyr Ser Glu Gly Glu Ser Ala Phe Pro Leu Asn Ser
1               5                   10                  15

Tyr Met Asn Ala
            20
```

<210> SEQ ID NO 39
<211> LENGTH: 20
<212> TYPE: PRT
<213> ORGANISM: Homo sapiens

<400> SEQUENCE: 39

Ala Ala Tyr Tyr Ser Glu Gly Glu Ser Ala Phe Pro Leu Asn Ser Tyr
1               5                   10                  15

Met Asn Ala Thr
            20

<210> SEQ ID NO 40
<211> LENGTH: 20
<212> TYPE: PRT
<213> ORGANISM: Homo sapiens

<400> SEQUENCE: 40

Ala Tyr Tyr Ser Glu Gly Glu Ser Ala Phe Pro Leu Asn Ser Tyr Met
1               5                   10                  15

Asn Ala Thr Asn
            20

<210> SEQ ID NO 41
<211> LENGTH: 20
<212> TYPE: PRT
<213> ORGANISM: Homo sapiens

<400> SEQUENCE: 41

Tyr Tyr Ser Glu Gly Glu Ser Ala Phe Pro Leu Asn Ser Tyr Met Asn
1               5                   10                  15

Ala Thr Asn His
            20

<210> SEQ ID NO 42
<211> LENGTH: 20
<212> TYPE: PRT
<213> ORGANISM: Homo sapiens

<400> SEQUENCE: 42

Tyr Ser Glu Gly Glu Ser Ala Phe Pro Leu Asn Ser Tyr Met Asn Ala
1               5                   10                  15

Thr Asn His Ala
            20

<210> SEQ ID NO 43
<211> LENGTH: 12
<212> TYPE: PRT
<213> ORGANISM: Homo sapiens

<400> SEQUENCE: 43

Tyr Ser Glu Gly Glu Ser Ala Phe Pro Leu Asn Ser
1               5                   10

<210> SEQ ID NO 44
<211> LENGTH: 20
<212> TYPE: PRT
<213> ORGANISM: Homo sapiens

<400> SEQUENCE: 44

Ala Pro Glu Gly Tyr Ala Ala Tyr Tyr Ser Glu Gly Glu Ser Ala Phe
1               5                   10                  15

Pro Leu Asn Ser

```
                20

<210> SEQ ID NO 45
<211> LENGTH: 19
<212> TYPE: PRT
<213> ORGANISM: Homo sapiens

<400> SEQUENCE: 45

Pro Glu Gly Tyr Ala Ala Tyr Tyr Ser Glu Gly Glu Ser Ala Phe Pro
1               5                   10                  15

Leu Asn Ser

<210> SEQ ID NO 46
<211> LENGTH: 18
<212> TYPE: PRT
<213> ORGANISM: Homo sapiens

<400> SEQUENCE: 46

Glu Gly Tyr Ala Ala Tyr Tyr Ser Glu Gly Glu Ser Ala Phe Pro Leu
1               5                   10                  15

Asn Ser

<210> SEQ ID NO 47
<211> LENGTH: 17
<212> TYPE: PRT
<213> ORGANISM: Homo sapiens

<400> SEQUENCE: 47

Gly Tyr Ala Ala Tyr Tyr Ser Glu Gly Glu Ser Ala Phe Pro Leu Asn
1               5                   10                  15

Ser

<210> SEQ ID NO 48
<211> LENGTH: 16
<212> TYPE: PRT
<213> ORGANISM: Homo sapiens

<400> SEQUENCE: 48

Tyr Ala Ala Tyr Tyr Ser Glu Gly Glu Ser Ala Phe Pro Leu Asn Ser
1               5                   10                  15

<210> SEQ ID NO 49
<211> LENGTH: 20
<212> TYPE: PRT
<213> ORGANISM: Homo sapiens

<400> SEQUENCE: 49

Ser Phe Ile Leu Lys Lys Val Leu Tyr Asp Arg Val Asn Asp Ser Ala
1               5                   10                  15

Asn Ile Tyr Ser
            20

<210> SEQ ID NO 50
<211> LENGTH: 15
<212> TYPE: PRT
<213> ORGANISM: Homo sapiens

<400> SEQUENCE: 50

Ala Ala Tyr Tyr Ser Glu Gly Glu Ser Ala Phe Pro Leu Asn Ser
1               5                   10                  15

<210> SEQ ID NO 51
```

```
<211> LENGTH: 14
<212> TYPE: PRT
<213> ORGANISM: Homo sapiens

<400> SEQUENCE: 51

Ala Tyr Tyr Ser Glu Gly Glu Ser Ala Phe Pro Leu Asn Ser
1               5                   10

<210> SEQ ID NO 52
<211> LENGTH: 13
<212> TYPE: PRT
<213> ORGANISM: Homo sapiens

<400> SEQUENCE: 52

Tyr Tyr Ser Glu Gly Glu Ser Ala Phe Pro Leu Asn Ser
1               5                   10

<210> SEQ ID NO 53
<211> LENGTH: 12
<212> TYPE: PRT
<213> ORGANISM: Homo sapiens

<400> SEQUENCE: 53

Tyr Ser Glu Gly Glu Ser Ala Phe Pro Leu Asn Ser
1               5                   10

<210> SEQ ID NO 54
<211> LENGTH: 13
<212> TYPE: PRT
<213> ORGANISM: Homo sapiens

<400> SEQUENCE: 54

Tyr Ser Glu Gly Glu Ser Ala Phe Pro Leu Asn Ser Tyr
1               5                   10

<210> SEQ ID NO 55
<211> LENGTH: 14
<212> TYPE: PRT
<213> ORGANISM: Homo sapiens

<400> SEQUENCE: 55

Tyr Ser Glu Gly Glu Ser Ala Phe Pro Leu Asn Ser Tyr Met
1               5                   10

<210> SEQ ID NO 56
<211> LENGTH: 15
<212> TYPE: PRT
<213> ORGANISM: Homo sapiens

<400> SEQUENCE: 56

Tyr Ser Glu Gly Glu Ser Ala Phe Pro Leu Asn Ser Tyr Met Asn
1               5                   10                  15

<210> SEQ ID NO 57
<211> LENGTH: 16
<212> TYPE: PRT
<213> ORGANISM: Homo sapiens

<400> SEQUENCE: 57

Tyr Ser Glu Gly Glu Ser Ala Phe Pro Leu Asn Ser Tyr Met Asn Ala
1               5                   10                  15

<210> SEQ ID NO 58
<211> LENGTH: 17
<212> TYPE: PRT
```

<213> ORGANISM: Homo sapiens

<400> SEQUENCE: 58

Tyr Ser Glu Gly Glu Ser Ala Phe Pro Leu Asn Ser Tyr Met Asn Ala
1               5                   10                  15

Thr

<210> SEQ ID NO 59
<211> LENGTH: 18
<212> TYPE: PRT
<213> ORGANISM: Homo sapiens

<400> SEQUENCE: 59

Tyr Ser Glu Gly Glu Ser Ala Phe Pro Leu Asn Ser Tyr Met Asn Ala
1               5                   10                  15

Thr Asn

<210> SEQ ID NO 60
<211> LENGTH: 19
<212> TYPE: PRT
<213> ORGANISM: Homo sapiens

<400> SEQUENCE: 60

Tyr Ser Glu Gly Glu Ser Ala Phe Pro Leu Asn Ser Tyr Met Asn Ala
1               5                   10                  15

Thr Asn His

<210> SEQ ID NO 61
<211> LENGTH: 20
<212> TYPE: PRT
<213> ORGANISM: Homo sapiens

<400> SEQUENCE: 61

Tyr Ser Glu Gly Glu Ser Ala Phe Pro Leu Asn Ser Tyr Met Asn Ala
1               5                   10                  15

Thr Asn His Ala
            20

<210> SEQ ID NO 62
<211> LENGTH: 28
<212> TYPE: PRT
<213> ORGANISM: Homo sapiens

<400> SEQUENCE: 62

Ala Pro Glu Gly Tyr Ala Ala Tyr Tyr Ser Glu Gly Glu Ser Ala Phe
1               5                   10                  15

Pro Leu Asn Ser Tyr Met Asn Ala Thr Asn His Ala
            20                  25

<210> SEQ ID NO 63
<211> LENGTH: 27
<212> TYPE: PRT
<213> ORGANISM: Homo sapiens

<400> SEQUENCE: 63

Pro Glu Gly Tyr Ala Ala Tyr Tyr Ser Glu Gly Glu Ser Ala Phe Pro
1               5                   10                  15

Leu Asn Ser Tyr Met Asn Ala Thr Asn His Ala
            20                  25

<210> SEQ ID NO 64

```
<211> LENGTH: 26
<212> TYPE: PRT
<213> ORGANISM: Homo sapiens

<400> SEQUENCE: 64

Glu Gly Tyr Ala Ala Tyr Tyr Ser Glu Gly Glu Ser Ala Phe Pro Leu
1               5                   10                  15

Asn Ser Tyr Met Asn Ala Thr Asn His Ala
            20                  25
```

METHOD FOR THE TREATMENT OR PREVENTION OF OSTEOARTHRITIS

FIELD OF THE INVENTION

The present invention is in the field of medicine and provides means and methods for the treatment, prevention or amelioration of osteoarthritis.

BACKGROUND OF THE INVENTION

Osteoarthritis (OA) is a type of joint disease that results from breakdown of joint cartilage and underlying bone, combined with an overall joint pathology including synovial inflammation and—fibrosis and meniscus pathology. The most common symptoms are joint pain and stiffness. Initially, symptoms may occur only following exercise, but over time may become constant. Other symptoms may include joint swelling, decreased range of motion, and when the back is affected by OA weakness or numbness of the arms and legs may present. The most commonly involved joints are those near the ends of the fingers, at the base of the thumb, neck, lower back, knees, and hips. Joints on one side of the body are often more affected than those on the other. Usually the problems come on over years. It can affect work and normal daily activities. Unlike other types of arthritis, only the joints are typically affected.

Causes include previous joint injury, abnormal joint or limb development abnormal alignment of joints and inherited factors. Risk is greater in those who are overweight, have one leg of a different length, and have jobs that result in high levels of joint stress. Osteoarthritis is believed to be caused by mechanical stress on the joint and low grade inflammatory processes. It develops as cartilage is lost with eventually the underlying bone becoming affected. The subchondral bone is also thought to be crucially involved in the etiology of the disease. As pain may make it difficult to exercise, muscle loss may occur. Diagnosis is typically based on signs and symptoms with medical imaging and other tests occasionally used to either support or rule out other problems. Unlike in rheumatoid arthritis, which is primarily an inflammatory condition, the joints do not typically become hot or red.

Treatment includes exercise, efforts to decrease joint stress, support groups, joint lubrication and (local) pain medications. Efforts to decrease joint stress include resting and the use of a cane. Weight loss may help in those who are overweight. Pain medications may include paracetamol (acetaminophen). If this does not work, orally administered NSAIDs such as naproxen may be used, or locally administered corticosteroids (eg triamcinolonacitonide) may be used, but these medications are associated with greater side effects. Opioids if used are generally only recommended short term due to the risk of addiction. If pain or movement restriction interferes with normal life despite other treatments, joint replacement surgery may help. An artificial joint, however, only lasts a limited amount of time and total joint replacement surgery is associated with severe complications like osteomyelitis. Outcomes for most people with osteoarthritis are good after total joint replacement.

OA is the most common form of arthritis with disease of the knee and hip affecting about 3.8% of people as of 2010. Among those over 60 years old about 10% of males and 18% of females are affected. It is the cause of about 2% of years lived with disability. In Australia about 1.9 million people are affected, and in the United States about 27 million people are affected. Before 45 years of age it is more common in men, while after 45 years of age it is more common in women. It becomes more common in both sexes as people become older.

While OA is a degenerative joint disease that may cause gross cartilage loss and morphological damage to other joint tissues, more subtle biochemical changes occur in the earliest stages of OA development. The water content of healthy cartilage is finely balanced by compressive force driving water out & swelling pressure drawing water in, supported by a distinct osmotic tissue pressure. Collagen fibers exert the compressive force, whereas the Gibbs-Donnan effect & cartilage proteoglycans create osmotic pressure which tends to draw water in.

However, during onset of OA, the collagen matrix becomes more disorganized and there is a decrease in proteoglycan content within cartilage. The breakdown of collagen fibers results in a net increase in water content. This increase occurs because whilst there is an overall loss of proteoglycans (and thus a decreased osmotic pull), it is outweighed by a loss of collagen. Without the protective effects of the proteoglycans, the collagen fibers of the cartilage can become susceptible to degradation and thus exacerbate the degeneration. Inflammation of the synovium (joint cavity lining) and the surrounding joint capsule can also occur, though often mild (compared to what occurs in rheumatoid arthritis).

Changes in the articular cartilage and articular chondrocytes that characterize OA resemble the cellular developmental process driving skeletal development by endochondral ossification. The analogy between endochondral ossification and OA progression has been widely recognized. Many of the cartilage-degrading enzymes that are excreted by hypertrophic chondrocytes in the growth plate are also central in progression and worsening of the OA condition. Also, well-known pathways controlling chondrocyte differentiation in the growth plate (RUNX2, COL10A1, ALP) are found active or deregulated in OA articular chondrocytes as well.

Other structures within the joint can also be affected. The ligaments within the joint become thickened and fibrotic and the menisci can become damaged and wear away. Menisci can be completely absent by the time a person undergoes a joint replacement. New bone outgrowths, called "spurs" or osteophytes, can form on the margins of the joints, possibly in an attempt to improve the congruence of the articular cartilage surfaces in the absence of the menisci. The subchondral bone volume increases and becomes less mineralized (osteoporotic/osteopenic). Also bone marrow lesions occur as a result of osteoarthritic changes in the subchondral bone. All these changes can cause problems in functioning and mechanical support for the overlying cartilage layer. The pain in an osteoarthritic joint has been related to thickened synovium and subchondral bone lesions.

Biochemically, OA is characterized by synthesis of extracellular matrix (ECM)-degrading enzymes, such as aggrecanases (a disintegrin and metalloproteinase with thrombospondine motifs (ADAMTSs)) and matrix metalloproteinases (MMPs), resulting in the active breakdown of the cartilage tissue matrix. The analogy between endochondral ossification and OA progression has been recognized and many of the cartilage degrading and mineralization enzymes that are secreted by hypertrophic chondrocytes in the growth plate are also crucially involved in OA.

Notwithstanding the progress made in the understanding of disease mechanisms, established and experimental treatment of OA is mainly symptomatic by alleviating pain and interfering with the cartilage degenerative processes to postpone total joint replacement.

SUMMARY OF THE INVENTION

The invention relates to a peptide derived from the full length human protein called bone morphogenetic protein-7 (BMP-7) for use in the treatment, amelioration or prevention of osteoarthritis. More in particular, the invention relates to a peptide for use in the treatment, amelioration or prevention of osteoarthritis wherein the peptide consists of an amino acid sequence according to SEQ ID NO: 18 or an analogue thereof, wherein the analogue consists of an amino acid sequence according to formula 1, or a fragment thereof wherein the fragment consists of at least 10 consecutive amino acids of SEQ ID NO: 18 or an amino acid sequence according to formula 1.

```
Formula 1:
                                              (SEQ ID NO: 29)
P K P S S X1 P X2 X3 L X4 X5 I X6 V X7 X8 X9 D X10

X11 X12 X13 X14 X15 X16 X17 X18 X19 X20 X21 M V V

X22 X23 S G S X24,
``` wherein;
X1=A or V
X2=T or D or E
X3=Q or D or K or S
X4=N or D or E or H
X5=A or D or S
X6=S or I or L or M or F or Y or E or H or K or Q or R or D
X7=L or E or K or T or M or R
X8=Y or A or D or E or H or K or S or T
X9=F or H or A or D or E or K or Q or R or Y
X10=D or I or L or E or N or S or T
X11=S or D or E or N or R
X12=S or D or E or K or N or T
X13=N or E or Q or R
X14=V or A or D or N or R or T or M or Y or H
X15=I or A or D or E or K or N or Q or R or S or T or V
X16=L or A or E or K or Q
X17=K or D or E or G or Q or R or W
X18=K or A or D or E or H or N or P or Q or S or T or I or V or M
X19=Y or D or E or H or K or Q or I or R
X20=R or D or E or K or N or S
X21=N or D
X22=R or E or S or D or K or Q or L
X23=A or E or D or S
X24=H or R.
Wherein X [#] indicates an amino acid position in the human BMP-7 protein that is variable.

DETAILED DESCRIPTION OF THE INVENTION

Osteoarthritic chondrocytes display a typical phenotype that is characterized by decreased expression of chondrogenic genes SOX9, COL2A1, ACAN and BAPX1/NKX3.2 and an increased expression of hypertrophic genes RUNX2, COL10A1, ALP, and an increased expression of genes encoding cartilage matrix degrading enzymes MMP13, ADAMTS5 and inflammatory genes COX-2 and IL-6 (FIG. 1). We show herein that a protein called bone morphogenetic protein-7 (BMP-7, also called OP-1) is capable of rescuing the OA phenotype (FIG. 1). Ours and earlier studies [22,23] addressing the disease-modifying properties of BMP-7 show that it decreases MMP13 expression in IL-1β-exposed chondrocytes, stimulates proteoglycan synthesis in OA chondrocytes, counteracts inflammatory cytokines (e.g. IL-1β) and induces an anabolic response in healthy chondrocytes. Intra-articular administration of BMP-7 protects against OA development and delays progression of OA in rats. A phase-1 clinical trial has been completed in OA patients and reported no serious adverse events after intra-articular injection of BMP-7. In accordance with this, the data reported herein unveil that BMP-7 actively suppresses the (OA) chondrocyte hypertrophic phenotype (FIG. 1).

Despite these promising results, intra-articular use of full-length recombinant human BMP-7 for OA-treatment may not be suitable for clinical use. Pre-clinical testing showed that weekly intra-articular BMP-7 injections were necessary to acquire a relevant result. This high frequency of intra-articular injections is not acceptable for clinical use due to risk of septic arthritis and patient discomfort. While a solution to prevent frequent intra-articular injections would encompass the encapsulation of BMP-7 in an intra-articular release system for long-term controlled release, retaining bioactivity of BMP-7 will pose an enormous challenge due to the denaturing conditions that generally apply for the production process of currently existing controlled-release systems. OA synovial fluid, in which BMP-7 is likely to be delivered, is a harsh hydrolytic and proteolytic environment that is expected to cause rapid degradation of the administered BMP-7. Finally, production of GMP-grade BMP-7 is technologically demanding with accompanying high costs.

To safeguard and enable the clinical use of the highly favourable characteristics of BMP-7 activity for OA-treatment, we sought for BMP-7 molecular mimics that are better compatible with the harsh OA synovial fluid environment and can potentially be incorporated in intra-articular molecular release systems for long-term release. For that reason we set out to prepare a set of overlapping 20-mer peptides (table 1) that collectively cover the entire mature BMP-7 polypeptide of 139 amino acids (SEQ ID NO: 27, table 3). The results confirmed earlier findings [20, 21] in that none of the peptides mimicked the potential of BMP-7 to rescue the OA phenotype. In more detail:, all peptides shown in table 1 were tested for expression of genes IL-6, ADAMTS5, COL10A, ALP, BAPX1/NKX3.2 and RUNX2 and found to evoke pro-hypertrophic, pro-mineralizing, pro-katabolic and pro-inflammatory responses. This was not unexpected, since pro-mineralizing/pro-osteogenic peptides have been described from BMP-2 [20, 32] and BMP-7 [21, 31].

Surprisingly, however, when we synthesized overlapping 20-mer peptides from a region constituted by amino acids 93-139 (SEQ ID NO: 1) of the mature human BMP-7 and replaced the Cysteine residues in that region with Serine residues (SEQ ID NO: 28, table 3), we found that peptides from the region formed by amino acids 100-139 were active as pro-chondrogenic and anti-inflammatory agents. A selection of peptides from this region was identified before as osteogenic agents, useful for inducing bone formation [31]. This region of amino acids 100-139 of the human BMP-7 polypeptide is further referred to herein as "region B".

Table 2 shows the results of expression analysis of several genes in the presence of several peptides for use according to the invention. Further details are provided in the Examples section.

In more detail; peptides shown in table 2 were tested for expression of genes IL-6, ADAMTS5, COL10A, ALP, BAPX1/NKX3.2 and RUNX2. Much to our surprise, we found that peptides with an amino acid sequence corresponding to amino acids 100-139 of BMP-7 or fragments thereof evoked the sought-after BMP-7-mimicking activity. This means that they induced a pro-chondrogenic and anti-inflammatory response. This was unexpected, since so far only pro-mineralizing and pro-osteogenic peptides have been described from BMP-2 [20] and BMP-7 [21].

TABLE 3

Amino acid sequence of mature BMP-7, Cysteine and Serine residues underlined.

| Name | Amino Acid Sequence | SEQ ID NO: |
|---|---|---|
| Mature BMP-7 | STGSKQRSQN RSKTPKNQEA LRMANVAENS SSDQRQACKK HELYVSFRDL GWQDWIIAPE GYAAYYCEGE CAFPLNSYMN ATNHAIVQTL VHFINPETVP KPCCAPTQLN AISVLYFDDS SNVILKKYRN MVVRACGCH | 27 |
| Mature BMP-7 with Cysteine replaced by Serine | STGSKQRSQN RSKTPKNQEA LRMANVAENS SSDQRQASKK HELYVSFRDL GWQDWIIAPE GYAAYYSEGE SAFPLNSYMN ATNHAIVQTL VHFINPETVP KPSSAPTQLN AISVLYFDDS SNVILKKYRN MVVRASGSH | 28 |

Consecutive and overlapping peptides from region B caused significantly decreased expression of OA chondrocyte phenotypic markers IL-6, ADAMTS5, COL10A, ALP and RUNX2 (annotated as "+" in table 2, as well as increased expression of chondrogenic marker BAPX1/NKX3.2 (annotated as "+" in table 2) in OA articular chondrocytes (Table 2).

Since 10-mer peptides from this region were previously shown to be active in increasing osteoblast proliferation and promoting osteoblast calcium deposition [21], it may safely be assumed that peptides of this length will also be useful in the present invention. In another embodiment of the invention, the peptides may advantageously be longer, such as 11, 12, 13, 14, 15, 16, 17, 18, 19 or 20 or more amino acids long. Longer peptides may also be employed, such as peptides of more than 21 amino acids such as more than 22, 23, 24, 25, 26, 27, 28, 29, 30, 31, 32, 33, 34, 35, 36, 37, or more than 38, such as 39 or 40 amino acids.

In one aspect, the invention therefore relates to a peptide for use in the treatment, amelioration or prevention of osteoarthritis, wherein the peptide comprises an amino acid sequence of at least 10 consecutive amino acids selected from the sequence according to SEQ ID NO: 18. This is deduced from the results shown in table 2.

Our experiments also revealed that the peptide has a maximum length of 40 amino acids or thereabout. The peptide for use according to the invention is preferably fully contained in the C-terminal 40 amino acids of BMP-7 (SEQ ID NO: 18). Every peptide that had an additional amino acid N-terminal of position 100 (the N-terminus of SEQ ID NO: 18) lost its activity in the assays as employed herein (table 2, see for example peptides with amino acid sequence according to SEQ ID NO: 2, 3, 4 and 5).

Of course, this description should not be interpreted so narrowly that there is no variation allowed in the peptides for use in the invention as described above. The skilled person is aware of the fact that the conformation of the peptide is conserved even when one or more, such as two, three, four or even five amino acids are changed, in particular when these changes relate to conservative amino acid substitutions. These peptides are known in the art as homologous peptides. Hence, the term "homologues" or "analogues" as used herein refers to peptides that retain their activity but differ with respect to their amino acid sequence. Homologues or analogues can be 75% identical with the sequences according to SEQ ID NO: 18 or fragments thereof or more, such as 77, 79, 80, 81, 82, 83, 84, 85, 86, 87, 88, 89, 90, 91, 92, 93, 94, 95, 96, 97, 98 or 99% identical.

As used herein, the degree of identity between two or more amino acid sequences is equivalent to a function of the number of identical positions shared by the sequences (i.e., % identity=number of identical positions divided by the total number of positions×100), excluding gaps, which need to be introduced for optimal alignment of the two sequences, and overhangs. The comparison of sequences and determination of percent identity between two or more sequences can be accomplished using standard methods known in the art. For example, a freeware conventionally used for this purpose is "Align" tool at NCBI recourse http://blast.ncbi.nlm.nih.gov/Blast.cgi?PAGE_TYPE=BlastSearch&BLAST_SPEC=blast2seq&LINK_LOC=align2seq In a preferred embodiment, the alignment of two sequences is to be performed over the full length of the polypeptides.

As used herein, the term "may" encompasses the word "can," and the term "may be" encompasses the words "is" or "are," depending on context. Furthermore, presence of the word "may" is intended to explain options for practicing or implementing the disclosure, without limitation.

We concluded that human BMP-7-derived peptides as described herein are able to mimic the favourable characteristics of the full-length human BMP-7 protein on the OA chondrocyte phenotype.

We have therewith determined the location and nature of the OA phenotype-suppressive action of BMP-7, whereas peptides from other regions in BMP-7 displayed no activity or pro-mineralizing/-hypertrophic actions. The bioactive potency of the candidate peptides was unexpectedly high. Independent of the tested concentration (1000, 100, 10 and 1 nanoMolar (nM) were tested), almost all region-B peptides induced similar fold-change gene expression magnitude differences in the screening, whereas a random control peptide with amino acid sequence SFILKKVLYDRVND-SANIYS (SEQ ID NO: 49) did not.

BMP-7 has unique OA chondrocyte-phenotype suppressive actions (FIG. 1). This action is most pronounced when a BMP-7 concentration is used around 1 nM. BMP-7 concentrations higher than 1 nM (eg 10 nM or 100 nM) have opposite and negative effects on the chondrocyte phenotype and thus unfavorably cause increased levels of hypertrophy, increased mineralisation, increased expression of cartilage breakdown genes and increased expression of inflammatory genes. Without wanting to be bound by theory, we speculate that BMP-7 incorporates a dual activity that is dependent on the concentration of BMP-7.

Surprisingly and in contrast with the full-length BMP-7 polypeptide, the 20-mer peptides according to SEQ ID NOs: 6, 7, 8, 9, 10, 11, 12, 13, 14, 15, and 17 efficiently suppressed the OA chondrocyte phenotype, independent of the tested concentration (1000, 100, 10 and 1 nM were tested). With this we have unexpectedly identified the region comprising the favorable OA phenotype-suppressive bioactivity of BMP-7, while peptides from other regions in BMP-7 displayed pro-mineralizing, pro-hypertrophic, pro-katabolic and pro-inflammatory actions.

Next to the 24 hours to which OA chondrocytes were exposed to individual peptides, the OA phenotype-suppressive action of the candidate peptides was highly effective when peptides were supplemented to OA chondrocyte cultures every second until day 10 in culture. Surprisingly, the OA phenotype-suppressive action of the peptides for use according to the invention even lasted up to 8 days in culture after a single initial 48-hours exposure.

The highly potent bioactivity at nanomolar-range concentration is at least similar to full-length mature BMP-7 and is a therapeutically important determinant, showing that the peptides for use in the invention are indeed powerful BMP-7 mimics for OA therapeutical use.

In addition to the action of the peptides for use in the invention on OA chondrocytes, the candidate peptides displayed biologically similar actions in an in vitro model for chondrogenic differentiation. Remarkably, eight days of single exposure, and even more pronounced with continuous peptide exposure of differentiating chondroprogenitor cells (ATDC5), solidly decreased the expression of hypertrophy and mineralization markers, while aggrecan expression (healthy chondrocyte marker) and BAPX1/NKX3.2 expression (anti-hypertrophy factor) was even further increased under continuous exposure to the peptides for use according to the invention.

Taken together, the peptides for use according to the invention lower the inflammatory OA chondrocyte phenotype, while at the same time supporting a pro-chondrogenic action on OA chondrocytes and healthy chondrocytes. In contrast to the full-length mature BMP-7 protein, peptides may advantageously be used in therapy because they are in general less susceptible for conformational and enzymatic inactivation. Peptides can be biochemically fine-tuned to increase their stability and activity; functionalized for carriers; are much smaller and thus suitable for incorporation in application-dedicated release systems for long-term intra-articular release.

Variants of the peptides as described above may be synthesized that are more resistant to degradation in proteolytic degradation in synovial fluid. Also, variants may be prepared that are more conformationally restricted and thus be more bioactive as compared to their original lead sequences. Such is well within reach for a skilled person, and requires only routine techniques now that the region B has been identified as the active region for the anabolic activity of BMP-7.

Such variants may include linear peptides, linear retro inverso peptides, retro-inverso peptides, cyclic peptides, mono-looped peptides, and two-looped peptides. CLIPS technology enables the routine production of such peptides (http://www.pepscan.com/therapeutics/clips-platform).

Two-looped peptides may contain two identical peptides as described herein or two different peptides as described herein.

An L-peptide has three analogue sequences built from L and D amino acids: the D-enantiomer or inverso-peptide with the same sequence, but composed of D-amino acids and a mirror conformation; the retro-peptide, consisting of the same sequence of L amino acids but in reverse order; and the retro-inverso or D-retro-enantiomer peptide, consisting of D-amino acids in the reversed sequence. While the L-peptide and its D-enantiomer are mirror structures of each other, the L-retro-peptide is the mirror image of the D-retro-inverso-peptide. On the other hand, the L-peptide and the D-retro-inverso-peptide share a similar arrangement of side-chains, although their carboxyl and amino groups point in opposing directions. For small peptides that do not depend on a secondary structure for binding, an L-peptide and its D-retro-inverso-peptide is likely to have a similar binding affinity with a target L-protein.

Peptides may be more active when they are looped, such as cyclic peptides. Such peptides may also be more stable and resistant to proteolytic degradation.

Such peptides and polypeptides may be more stable in an environment hostile to linear polypeptides, such as a hydrolytic or proteolytic environment. In particular for therapeutic purposes, it may be advantageous to use more stable peptides, such as the ones mentioned above. Hence, the invention also relates to the use of peptides selected from the group consisting of linear peptides, linear retro-inverso peptides, retro-inverso peptides, cyclic peptides, mono-looped peptides, and two-looped peptides.

Ways to render a peptide less susceptible to degradation are known in the art, such as the inclusion of one or more non-natural amino acids, such as the D-enantiomer of an L-amino acid and the retro orientation of the peptide backbone in the retro-inverso variant. These peptides are non-natural, hence natural proteases are not able to cleave them.

Means and methods for increasing the bioactivity of the peptides for use according to the invention are also known in the art. Examples of such techniques are cyclization and looping of the peptides, which provides a more constraint conformational context of essential amino acid residues.

Patent application US2006/0058231 discloses BMP-7 variants with improved properties. This document is hereby incorporated by reference. US2006/0058231 discloses that some amino acids of BMP-7 may be substituted with other amino acids without affecting the function of the BMP-7 protein.

Among the improved properties of BMP-7 as a result of the above mentioned amino acid substitutions are: increased expression yield, expression in the absence of a pro-domain, increased solubility, increased stability, increased specific biological activity, altered receptor specificity, altered receptor binding affinity, altered co-receptor specificity, altered co-receptor binding affinity, increased binding to noggin, reduced binding to noggin and decreased immunogenicity, With respect to the region B amino acids, this means that amino acids at positions 6, 8, 9, 11, 12, 14, 16-18, 20-31, 35, 36 and 40 of SEQ ID NO: 18 may be altered or substituted, without affecting the activity of BMP-7. In some instances, these amendments (amino acid substitutions), even improved the activity of BMP-7.

The region corresponding to SEQ ID NO: 18 may therefore also be described as shown in formula 1:

```
Formula 1:
                                                    (SEQ ID NO: 29)
P K P S S X1 P X2 X3 L X4 X5 I X6 V X7 X8 X9 D X10

X11 X12 X13 X14 X15 X16 X17 X18 X19 X20 X21 M V V

X22 X23 S G S X24,
``` wherein;
X1=A or V
X2=T or D or E
X3=Q or D or K or S
X4=N or D or E or H
X5=A or D or S
X6=S or I or L or M or F or Y or E or H or K or Q or R or D X7=L or E or K or T or M or R
X8=Y or A or D or E or H or K or S or T
X9=F or H or A or D or E or K or Q or R or Y
X10=D or I or L or E or N or S or T
X11=S or D or E or N or R
X12=S or D or E or K or N or T
X13=N or E or Q or R
X14=V or A or D or N or R or T or M or Y or H
X15=I or A or D or E or K or N or Q or R or S or T or V
X16=L or A or E or K or Q
X17=K or D or E or G or Q or R or W
X18=K or A or D or E or H or N or P or Q or S or T or I or V or M
X19=Y or D or E or H or K or Q or I or R
X20=R or D or E or K or N or S
X21=N or D
X22=R or E or S or D or K or Q or L
X23=A or E or D or S
X24=H or R.

The above peptides according to formula 1 may be regarded as equivalents or variants or analogues of the peptide according to SEQ ID NO: 18. In one embodiment of the invention, a variant of SEQ ID NO: 18 comprises 24, 23, 22, 21, 20, 19, 18, 17, 16, 15, 14, 13, 12, 11, 10, 9, 8, 7, 6, 5, 4, 3, 2 or 1 amino acid substitution(s) selected from the group consisting of substitutions X1, X2, X3, X4, X5, X6, X7, X8, X9, X10, X11, X12, X13, X14, X15, X16, X17, X18, X19, X29, X21, X22, X23 and X24.

The amino acids in bold print and underlined in formula 1 represent the amino acids in the peptides according to SEQ ID NO: 18 (wild type sequence) that should preferably not be changed or substituted. The preferred amino acids at positions X1-X24 are underlined. These represent the wild type amino acids at the corresponding positions.

In addition, we tested the region B peptides according to SEQ ID NO: 6-17 for their OA chondrocyte phenotype changing properties and found that they also increased the expression of genes SOX9 and COL2A1 and decreased the expression of COX-2 (Table 5).

In addition to the above described region B, we also found that peptides from another region (amino acids 58-85 of the mature BMP-7 protein) could advantageously be used to mimic the favorable actions of BMP-7 in OA. Peptides from that region even synergistically improved the actions of the peptides from the B region described above. This second region is herein described as region A. Peptides from that region A are therewith useful in the treatment, amelioration or prevention of osteoarthritis in combination with the peptides from region B.

Peptides from this region A may be described as consisting of an amino acid sequence of between 12 and 28 amino acids in length comprising an amino acid sequence according to SEQ ID NO: 30 (YSEGESAFPLNS) or a variant thereof according to formula 2 (SEQ ID NO: 31), wherein the amino acid sequence of said peptide is comprised in SEQ ID NO: 32 (APEGYAAYYSEGESAFPLNSYMNATNHA) or a variant thereof according to formula 3 (SEQ ID NO: 33).

Formula 3:
(SEQ ID NO: 33)
Z1 Z2 Z3 G Y Z4 A Z5 Y S E G Z6 S Z7 Z8 Z9 L Z10 Z11 Z12 M N A T Z13 H A wherein
Z1=A or I or L or M or Y or V or E or H or K or Q or R,
Z2=P or Y or M,
Z3=E or R or H or K or N or P or Q or S or T or I or L or M or V,
Z4=A or E or Q or R or S,
Z5=Y or N or D,
Z6=E or A or Q,
Z7=A or D or E or H or K or S,
Z8=F or A or D or E or H or Q or R or S,
Z9=P or M,
Z10=N or A or D or S or T or E or Q or R or I or V,
Z11=S or A or D or E or H or K or N or P or Q or T,
Z12=Y or H or D or G or H or N or R or S or T or wherein
Z13=N or F or W or Y or H or K or R.

The above peptides according to formula 3 may be regarded as equivalents or variants of the peptide according to SEQ ID NO: 32. In one embodiment of the invention, a variant of SEQ ID NO: 32 comprises 12, 11, 10, 9, 8, 7, 6, 5, 4, 3, 2 or 1 amino acid substitution selected from the group consisting of substitutions Z1, Z2, Z3, Z4, Z5, Z6, Z7, Z8, Z9, Z10, Z11, Z12 and Z13.

Accordingly, variants of the region corresponding to SEQ ID NO: 30 may therefore also be described as shown in formula 2:

Formula 2:
(SEQ ID NO: 31)
Y S E G Z6 S Z7 Z8 Z9 L Z10 Z11 wherein
Z6=E or A or Q,
Z7=A or D or E or H or K or S,
Z8=F or A or D or E or H or Q or R or S,
Z9=P or M,
Z10=N or A or D or S or T or E or Q or R or I or V or wherein
Z11=S or A or D or E or H or K or N or P or Q or T.

Examples of suitable peptides from the A region are exemplified in Table 4.

Preferred variants may include linear peptides, linear retro inverso peptides, retro-inverso peptides, cyclic peptides, mono-looped peptides, and two-looped peptides. CLIPS technology enables the routine production of such peptides (http://www.pepscan.com/therapeutics/clips-platform). Two-looped peptides may contain two identical peptides from region A or B as described herein or two different peptides from region A or B or combinations thereof as described herein. Particularly preferred are two-looped peptides with one loop comprising a peptide from the A region as described herein and an other loop comprising a peptide from the B region as described herein.

TABLE 4

Peptides from region A suitable for use in the treatment of OA in combination with peptides from region B.

| SEQ ID NO: | Amino acid sequence |
| --- | --- |
| 34 | APEGYAAYYSEGESAFPLNS |
| 35 | PEGYAAYYSEGESAFPLNSY |
| 36 | EGYAAYYSEGESAFPLNSYM |
| 37 | GYAAYYSEGESAFPLNSYMN |
| 38 | YAAYYSEGESAFPLNSYMNA |

TABLE 4-continued

Peptides from region A suitable for use in the treatment of OA in combination with peptides from region B.

| SEQ ID NO: | Amino acid sequence |
|---|---|
| 39 | AAYYSEGESAFPLNSYMNAT |
| 40 | AYYSEGESAFPLNSYMNATN |
| 41 | YYSEGESAFPLNSYMNATNH |
| 42 | YSEGESAFPLNSYMNATNHA |
| 43 | YSEGESAFPLNS |
| 44 | APEGYAAYYSEGESAFPLNS |
| 45 | PEGYAAYYSEGESAFPLNS |
| 46 | EGYAAYYSEGESAFPLNS |
| 47 | GYAAYYSEGESAFPLNS |
| 48 | YAAYYSEGESAFPLNS |
| 50 | AAYYSEGESAFPLNS |
| 51 | AYYSEGESAFPLNS |
| 52 | YYSEGESAFPLNS |
| 53 | YSEGESAFPLNS |
| 54 | YSEGESAFPLNSY |
| 55 | YSEGESAFPLNSYM |
| 56 | YSEGESAFPLNSYMN |
| 57 | YSEGESAFPLNSYMNA |
| 58 | YSEGESAFPLNSYMNAT |
| 59 | YSEGESAFPLNSYMNATN |
| 60 | YSEGESAFPLNSYMNATNH |
| 61 | YSEGESAFPLNSYMNATNHA |
| 62 | APEGYAAYYSEGESAFPLNSYMNATNHA |
| 63 | PEGYAAYYSEGESAFPLNSYMNATNHA |
| 64 | EGYAAYYSEGESAFPLNSYMNATNHA |

TABLE 1

Human BMP-7 spanning consecutive 20-mer peptides with at least 2 amino acids overlap between peptides and their OA chondrocyte phenotype changing properties.

| Peptide sequence | SEQ ID | IL-6 | ADAMTS5 | COL10A | BAPX1/NKX3.2 | ALP | RUNX2 |
|---|---|---|---|---|---|---|---|
| STGSKQRSQNRSKTPKNQEA | 19 | - | - | - | - | - | - |
| KTPKNQEALRMANVAENSSS | 20 | - | - | - | - | - | - |
| SSDQRQACKKHELYVSFRDL | 21 | - | - | - | - | - | - |
| DLGWQDWIIAPEGYAAYYCE | 22 | - | - | - | - | - | - |
| CEGECAFPLNSYMNATNHAI | 23 | - | - | - | - | - | - |
| AIVQTLVHFINPETVPKPCC | 24 | - | - | - | - | - | - |
| CCAPTQLNAISVLYFDDSSN | 25 | - | - | - | - | - | - |
| SSNVILKKYRNMVVRACGCH | 26 | - | - | - | - | - | - |

[−] denotes the absence of a significant effect or a significantly decreased expression of chondrogenic marker genes BAPK1/NKX3.2, or a significantly increased expression of OA phenotypic markers IL-6, ADAMTS5, COL10A, ALP and RUNX2 in OA articular chondrocytes, in comparison to untreated OA articular chondrocytes.

TABLE 2

Human BMP-7 derived consecutive 20-mer peptides with cysteine residues substituted to serine and their OA chondrocyte phenotype changing properties. Results are visualized in FIGS. 2-7.

| Peptide sequence | SEQ ID NO: | IL-6 | ADAMTS5 | COL10A | BAPX1/NKX3.2 | ALP | RUNX2 |
|---|---|---|---|---|---|---|---|
| FINPETVPKPSSAPTQLNAISVLYFDDSSNVILKKYRNMVVRASGSH | 1 | - | - | - | - | - | - |
| FINPETVPKPSSAPTQLNAI | 2 | - | - | - | - | - | - |
| NPETVPKPSSAPTQLNAISV | 3 | - | - | - | - | - | - |
| ETVPKPSSAPTQLNAISVLY | 4 | - | - | - | - | - | - |

TABLE 2-continued

Human BMP-7 derived consecutive 20-mer peptides with cysteine
residues substituted to serine and their OA chondrocyte phenotype
changing properties. Results are visualized in FIGS. 2-7.

| Peptide sequence | SEQ ID NO: | IL-6 | ADAMTS5 | COL10A | BAPX1/NKX3.2 | ALP | RUNX2 |
|---|---|---|---|---|---|---|---|
| VPKPSSAPTQLNAISVLYFD | 5 | − | − | − | − | − | + |
| PKPSSAPTQLNAISVLYFDD | 6 | + | + | + | + | + | + |
| KPSSAPTQLNAISVLYFDDS | 7 | + | + | + | + | + | + |
| SSAPTQLNAISVLYFDDSSN | 8 | + | + | + | + | + | + |
| APTQLNAISVLYFDDSSNVI | 9 | + | + | − | + | + | + |
| TQLNAISVLYFDDSSNVILK | 10 | + | + | − | + | + | + |
| LNAISVLYFDDSSNVILKKY | 11 | + | + | + | + | + | + |
| AISVLYFDDSSNVILKKYRN | 12 | + | + | + | + | + | + |
| SVLYFDDSSNVILKKYRNMV | 13 | + | + | + | + | + | + |
| LYFDDSSNVILKKYRNMVVR | 14 | + | + | + | + | + | − |
| FDDSSNVILKKYRNMVVRAS | 15 | + | + | + | + | + | − |
| DSSNVILKKYRNMVVRASGS | 16 | + | + | + | + | + | − |
| SSNVILKKYRNMVVRASGSH | 17 | + | + | + | + | + | + |
| PKPSSAPTQLNAISVLYFDDSSNVILKKYRNMVVRASGSH | 18 | + | + | + | + | + | + |

[+] denotes a significantly increased expression of chondrogenic marker gene BAPX1/NKX3.2, or a significantly decreased expression of OA phenotypic markers IL-6, ADAMTS5, COL10A, ALP and RUNX2 in OA articular chondrocytes, in comparison to untreated OA articular chondrocytes.
[−] denotes the absence of a significant effect or a significantly decreased expression of chondrogenic marker genes BAPX1/NKX3.2, or a significantly increased expression of OA phenotypic markers IL-6, ADAMTS5, COL10A, ALP and RUNX2 in OA articular chondrocytes, in comparison to untreated OA articular chondrocytes.
A peptide was considered as having OA chondrocyte phenotype suppressive activity when at least 5 out of 6 markers were positive (+). Those peptides were shown in bold.

TABLE 5

Human BMP-7 derived consecutive 20-mer peptides with cysteine residues substituted
to serine and their OA chondrocyte phenotype changing properties.

| Peptide sequence | SEQ ID No: | COX-2 | COL2A1 | SOX9 |
|---|---|---|---|---|
| PKPSSAPTQLNAISVLYFDD | 6 | + | + | + |
| KPSSAPTQLNAISVLYFDDS | 7 | + | + | + |
| SSAPTQLNAISVLYFDDSSN | 8 | + | + | + |
| APTQLNAISVLYFDDSSNVI | 9 | + | + | + |
| TQLNAISVLYFDDSSNVILK | 10 | + | + | + |
| LNAISVLYFDDSSNVILKKY | 11 | + | + | + |
| AISVLYFDDSSNVILKKYRN | 12 | + | + | + |
| SVLYFDDSSNVILKKYRNMV | 13 | + | + | + |
| LYFDDSSNVILKKYRNMVVR | 14 | + | + | + |
| FDDSSNVILKKYRNMVVRAS | 15 | + | + | + |
| DSSNVILKKYRNMVVRASGS | 16 | + | + | + |
| SSNVILKKYRNMVVRASGSH | 17 | + | + | + |

[+] denotes a significantly increased expression of chondrogenic marker genes SOX9 and COL2A1, or a significantly decreased expression of OA phenotypic marker COX-2 in OA articular chondrocytes, in comparison to untreated OA articular chondrocytes.

LEGEND TO THE FIGURES

FIG. 1: BMP-7 rescues OA-associated chondrocyte phenotype.

Osteoarthritis chondrocytes display a typical phenotype that is characterized by decreased expression of SOX9, COL2A1 and BAPX1/NKX3.2 and an increased expression of COX-2 and IL-6 mRNAs (see left panel). BMP-7 (1 nM) is able to rescue this OA-associated chondrocyte phenotype by normalizing expression of above genes (left panel).

Functional ALP enzyme activity in cell lysates and PGE2 secretion in the culture medium was also normalized upon BMP-7 treatment of OA chondrocytes (right panel).

Expression of indicated mRNAs was determined by RT-qPCR, relatively to control conditions (normalized for 28S rRNA expression). In graphs, error bars represent mean±SEM, statistical differences were calculated as compared to healthy condition. *=p<0.05.

FIGS. 2-7: Actions of BMP-7 derived peptides on primary human OA articular chondrocytes.

The action of 20-mer peptides (10 nM) of SEQ ID NO: 2-17 (peptides with 1 or 2 amino acids intervals (18-19 amino acid overlap)) and a random peptide with a sequence according to SEQ ID NO: 49 on the expression of the indicated genes was determined on a validated pool of passage 2 OA human articular chondrocytes (n=18) and compared to full-length recombinant BMP-7 (1 nM). Samples were harvested after 24 hours and analyzed for indicated genes by RT-qPCR (normalized for 28S rRNA expression and relative to control conditions (no peptide exposure)). In the graphs, numbers on the x-axis represent individual peptides according to their SEQ ID NO's:, error bars represent mean±SEM, statistical differences were calculated (one-way ANOVA with bonferroni correction) to control condition. *=p<0.05 lower than control condition for ADAMTS5, ALP, COL10A1, RUNX2, and IL-6 and higher than control condition for BAPX1/NKX3.2. Random peptide is a peptide according to SEQ ID NO: 49.

Figure 8:
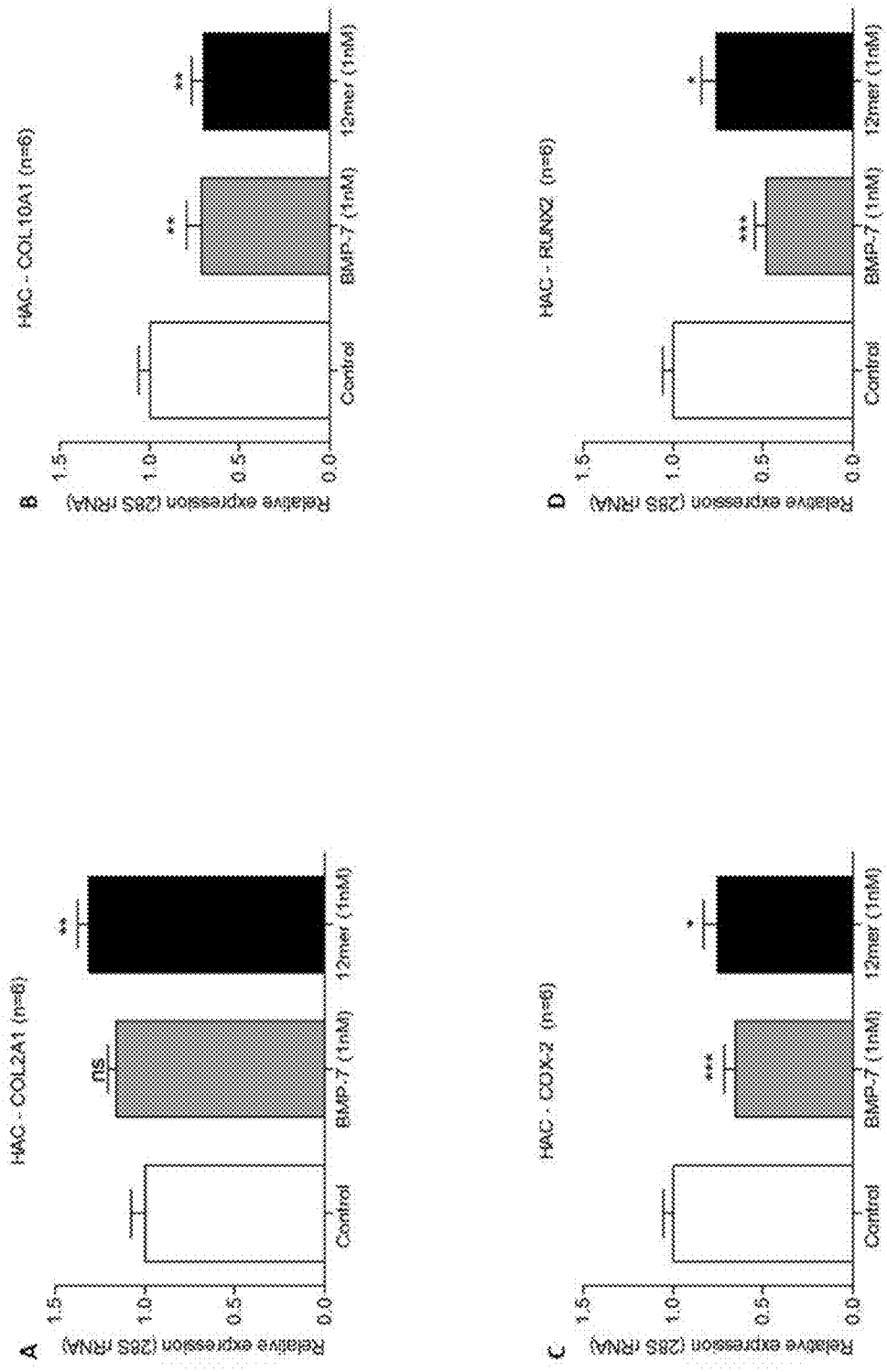

FIG. 8: Diagram showing relative expression of COL2A1, Col10A1, COX-2 and RUNX2 in isolated chondrocytes from OA patients in the presence of a control peptide, BMP-7 and a peptide according to SEQ ID NO: 43.

Figure 9:
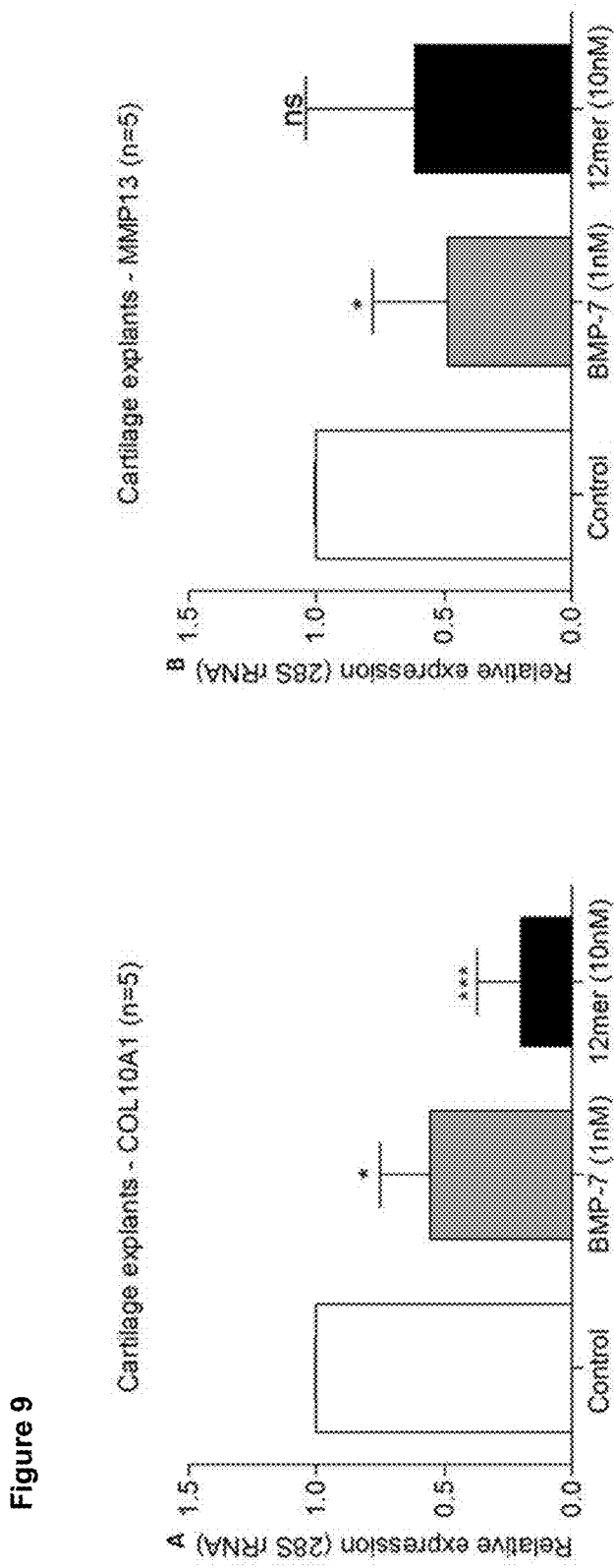

FIG. 9: Diagrams showing the relative expression of COL10A1 and MMP13 in cartilage explants from OA patients in the presence of a control peptide, BMP-7 and a peptide according to SEQ ID NO: 43.

EXAMPLES

Example 1

OA Chondrocyte Phenotype Suppressive Actions of BMP-7 Peptides in the Presence of OA Synovial Fluid We analysed candidate peptides from region B for their OA phenotype suppressive actions on primary OA articular chondrocytes in the presence of 20% (v/v) OA synovial fluid (SF). Data were combined from three individual OA chondrocyte isolates (n=3) that were each tested in triplicate. Seeded passage-2 OA chondrocytes were exposed to 100 nM of peptide in the absence or presence of OA synovial fluid and after 24 hours analysed for mRNA expression of genes IL-6, ADAMTS5, COL10A, ALP, BAPX1 and RUNX2 (corrected for 28S rRNA expression and relative to control conditions (no peptide exposure)).

Results were scored as + or − as shown in the footnotes of the tables.

Example 2

Hypertrophy Suppressive Action of BMP-7 Peptides during Chondrogenic Differentiation of ATDC5 Cells ATDC5 cells were differentiated using standard protocols for 8 days in the presence or absence of 1 nM and 10 nM peptides from region B. Peptides were added at start of differentiation and at every medium change (multiple) or only at start of differentiation and not during every medium change (single). At day 8 in differentiation, samples were harvested and analysed for gene expression by RT-qPCR (corrected for b-actin expression and relative to t=0).

Example 3

Evaluation of OA-suppressive Actions in Ex Vivo and In Vivo Models for OA

Peptides for use according to the invention may also be investigated in ex vivo testing: Full-thickness cartilage biopsies (3 mm punches) from femur condyles from TKA (K&L grade 2-3) may be freshly harvested directly after surgery, randomized per patient and taken into ex vivo culture as described previously. Biopsies from patients may be exposed to selected peptides after twenty-four hours at 0.1, 1, 10 or 100 nM for 7 days and medium may be changed daily with fresh peptide.

BMP-7 at 1 nM may be used as positive control and vehicle may be used as negative control. After exposure, the cartilage biopsies may be processed to address major cartilage quality-determining parameters. DNA content per wet-weight and GAG content may be determined. ALP enzyme activity may also be investigated. PGE2 and GAG secretion in the culture medium may be analyzed. Gene expression may be determined for major OA chondrocyte phenotype marker-genes as described herein.

Local OA-related changes in the biopsies as a result of exposure to the peptides may be analyzed by (immuno) histochemistry (alcian blue- and immunostainings for COL2A1, SOX9 and COX-2) to further support the notion that the peptides for use according to the invention are suitable for medical use in OA.

Diffusion and localization of the peptides into cartilage biopsies may be addressed in a similar set-up wherein a biotinylated variant of the peptides may be used. After culture these biopsies may be processed for histochemistry. Peptide that is diffused into the cartilage biopsies may be fluorescently visualized by Streptavidin-Alexafluor 488-mediated detection. This approach may also aid in visualizing the phenotypic context and localization of the peptide by MALDI-IMS and help to discriminate it from potential endogenous BMP-7 fragments.

Example 4

In Vivo Testing

Amino acid sequences of region-B are 100% homologous between human and mouse. In order to further establish the in vivo activity of the peptides for use according to the invention, representative peptides may be tested in a well-accepted model for post-traumatic OA, the DMM model.

The medial meniscus may be destabilized in 12 weeks old C57BL/6 mice. One week after DMM induction, peptides may be administered intra-articularly by twice-weekly injections as described previously. Dose may be based on intra-articular BMP-7 studies in which weekly injections of 250 ng BMP-7 in a rat knee joint (in 100 µl) showed favorable outcomes. As 10 µl can be injected in an OA mouse joint an equivalent amount of 25 ng peptide in this volume may be injected per knee joint. An amount of 2.5 and 0.25 ng peptide may also be tested in 2 additional groups to determine the pharmacological potency of the peptide. Saline injections may be used as controls. The sample size of this experiment is advantageously 8 mice per group. Animals may be sacrificed at consecutive time points after start of peptide treatment (2, 4, 8 weeks). Knee joints may be processed for (immuno)histochemical analyses and OARSI scoring (Safranin-O; modified Pritzker).

Example 5

Treatment of Isolated Chondrocytes from OA Patients

Isolated chondrocytes from OA patients (n=6) were treated with BMP-7 (1 nM) or the 12-mer peptide according to SEQ ID NO: 43 (1 nM) for 24 h. Pro-chondrogenic (FIG. 8A) and hypertrophic (FIGS. 8B, 8C and 8D) gene expression was determined via qRT-PCR and normalized for 28S rRNA levels. These results confirmed our previous findings that BMP-7 or the 12 mer peptide induced an upregulation of pro-chondrogenic genes, such as Col2a1 (A), and a downregulation of pro-hypertrophic genes, such as COL10A1, COX-2 and RUNX2 (B, C, D). These results show the BMP-7 mimicking bioactivity of the core sequence from the region-A peptide.

Example 6

Treatment of Cartilage Explants 4 mm2 cartilage explants were taken from non-lesion areas of OA patient's knee articular cartilage (n=5) and randomly assigned to different experimental treatment conditions (4 explants per treatment group). After a 24 h equilibration period the explants were treated with BMP-7 (1 nM) or the 12-mer peptide according to SEQ ID NO: 43 (10 nM) for 24 h. Hypertrophic gene expression was determined via qRT-PCR and normalized for 28S rRNA levels. After treatment with BMP-7 or the 12 mer we observed a downregulation of pro-hypertrophic genes, such as Co110a1 (FIG. 9A) and MMP13 (FIG. 9B). These results are in line with the effects described above and show the BMP-7 mimicking bioactivity of the peptides according to the invention.

Example 7

Staining of Cartilage Explants

Cartilage explants obtained from 2 patients were cultured for 14 days in the presence of BMP-7 (1 nM) or BMP-7 mimicking peptide SVLYFDDSSNVILKKYRNMV (SEQ ID NO: 13) at 10 nM. Glycosaminoglycans (GAGs), an important component of the extracellular matrix (ECM), were stained with Safranin-O (in red) and other tissues are counterstained with Fast green (in green/blue).

Both patients showed an increased Safranin-O intensity in BMP7 and peptide SVLYFDDSSNVILKKYRNMV (SEQ ID NO: 13) treated explants compared to control.

These results are in line with the effects described above and show the BMP-7 mimicking bioactivity of the peptides according to the invention.

Example 8

Treatment of Cartilage Explants

Cartilage explants of 3 mm$^2$ were taken from OA patient's knee cartilage (n=6) and treated with BMP-7 (1 nM), with peptide SVLYFDDSSNVILKKYRNMV (SEQ ID NO: 13) at 10 nM or a scrambled irrelevant control peptide (10 nM) for 14 days. Prostaglandin E2 (PGE2) levels, a pro-hypertrophic factor, were determined via an ELISA.

Synovial tissue samples from OA patients (n=6) were treated with BMP-7 (1 nM), with peptide SVLYFDDSSN-VILKKYRNMV (SEQ ID NO: 13) at 10 nM or a scrambled irrelevant control peptide (10 nM) for 24 h. PGE2 levels were determined via an ELISA.

Hoffa's fat pad tissue samples from OA patients (n=6) were treated with BMP-7 (1 nM) with peptide SVLYFDDSSNVILKKYRNMV (SEQ ID NO: 13) at 10 nM or a scrambled irrelevant control peptide (10 nM) for 24 h. PGE2 levels were determined via an ELISA.

Meniscus tissue samples from OA patients (n=6) were treated with BMP-7 (1 nM) with peptide peptide SVLYFDDSSNVILKKYRNMV (SEQ ID NO: 13) at 10 nM or a scrambled irrelevant control peptide (10 nM) for 24 h. PGE2 levels were determined via an ELISA.

The results unequivocally showed reduce PGE2 levels in the cartilage and the surrounding tissues after BMP-7 or peptide SVLYFDDSSNVILKKYRNMV (SEQ ID NO: 13) treatment. Treatment with the scrambled peptide did not result in a reduction of PGE2 levels.

These results are in line with the effects described above and show the BMP-7 mimicking bioactivity of the peptides according to the invention.

REFERENCES

1. Glyn-Jones, S; Palmer, A J; Agricola, R; Price, A J; Vincent, T L; Weinans, H; Carr, A J (3 March 2015). "Osteoarthritis.". Lancet 386: 376-87. doi:10.1016/50140-6736 (14)60802-3. PMID 25748615.
2. Berenbaum F (2013). "Osteoarthritis as an inflammatory disease (osteoarthritis is not osteoarthrosis!)". Osteoarthritis and Cartilage 21 (1): 16-21. doi:10.1016/j.joca.2012.11.012. PMID 23194896.
3. March, L; Smith, E U; Hoy, D G; Cross, M J; Sanchez-Riera, L; Blyth, F; Buchbinder, R; Vos, T; Woolf, A D (June 2014). "Burden of disability due to musculoskeletal (MSK) disorders.". Best practice & research. Clinical rheumatology 28 (3): 353-66. doi: 10.1016/j.berh.2014.08.002. PMID 25481420.
4. Maroudas A I (April 1976). "Balance between swelling pressure and collagen tension in normal and degenerate cartilage". Nature 260 (5554): 808-9. doi:10.1038/260808a0. PMID 1264261.
5. Bollet A J, Nance J L (July 1966). "Biochemical Findings in Normal and Osteoarthritic Articular Cartilage. II. Chondroitin Sulfate Concentration and Chain Length, Water, and Ash Content". J. Clin. Invest. 45 (7): 1170-7. doi:10.1172/JC1105423. PMC 292789. PMID 16695915.

6. Brocklehurst R, Bayliss M T, Maroudas A, Coysh H L, Freeman M A, Revell P A, Ali S Y (January 1984). "The composition of normal and osteoarthritic articular cartilage from human knee joints. With special reference to unicompartmental replacement and osteotomy of the knee". J Bone Joint Surg Am 66 (1): 95-106. PMID 6690447.
7. Chou M C, Tsai P H, Huang G S, Lee H S, Lee C H, Lin M H, Lin C Y, Chung H W (April 2009). "Correlation between the MR T2 value at 4.7 T and relative water content in articular cartilage in experimental osteoarthritis induced by ACL transection". Osteoarthr. Cartil. 17 (4): 441-7. doi:10.1016/j.joca.2008.09.009. PMID 18990590.
8. Grushko G, Schneiderman R, Maroudas A (1989). "Some biochemical and biophysical parameters for the study of the pathogenesis of osteoarthritis: a comparison between the processes of aging and degeneration in human hip cartilage". Connect. Tissue Res. 19 (2-4): 149-76. doi:10.3109/03008208909043895. PMID 2805680.
9. Mankin H J, Thrasher A Z (January 1975). "Water content and binding in normal and osteoarthritic human cartilage". J Bone Joint Surg Am 57 (1): 76-80. PMID 1123375.
10. Venn M, Maroudas A (April 1977). "Chemical composition and swelling of normal and osteoarthrotic femoral head cartilage. I. Chemical composition". Ann. Rheum. Dis. 36 (2): 121-9. doi:10.1136/ard.36.2.121. PMC 1006646. PMID 856064.
11. Madry H, Luyten F P, Facchini A (2012). "Biological aspects of early osteoarthritis". Knee Surg. Sports Traumatol. Arthrosc. 20 (3): 407-22. doi:10.1007/s00167-011-1705-8. PMID 22009557.
12. Englund M, Roemer F W, Hayashi D, Crema M D, Guermazi A (2012). "Meniscus pathology, osteoarthritis and the treatment controversy". Nat. Rev. Rheumatol. 8 (7): 412-9. doi:10.1038/nrrheum.2012.69. PMID 22614907.
13. Li G, Yin J, Gao J, Cheng T S, Pavlos N J, Zhang C, Zheng M H (2013). "Subchondral bone in osteoarthritis: insight into risk factors and microstructural changes". Arthritis Research & Therapy 15 (6): 223. doi:10.1186/ar4405. PMID 24321104.
14. Hill C L, Gale D G, Chaisson C E, Skinner K, Kazis L, Gale M E, Felson D T (2001). "Knee effusions, popliteal cysts, and synovial thickening: association with knee pain in osteoarthritis". J. Rheumatol. 28 (6): 1330-7. PMID 11409127.
15. Felson D T, Chaisson C E, Hill C L, Totterman S M, Gale M E, Skinner K M, Kazis L, Gale D R (3 Apr. 2001). "The association of bone marrow lesions with pain in knee osteoarthritis". Ann Intern Med 134 (7): 541-9. doi:10.7326/0003-4819-134-7-200104030-00007. PMID 11281736
16. Sofat, N. Int J Exp Pathol 90, 463-479, (2009).
17. Dreier, R. Arthritis Res Ther 12, 216, (2010).
18. Tchetina, E. V. Arthritis 2011, 683970, (2011).
19. van der Kraan, P. M. et. al. Osteoarthritis and cartilage 20, 223-232, (2012).
20. Saito, A., Suzuki, Y., Ogata, S., Ohtsuki, C. & Tanihara, M. Accelerated bone repair with the use of a synthetic BMP-2-derived peptide and bone-marrow stromal cells. J Biomed Mater Res A 72, 77-82, doi: 10.1002/jbm.a.30208 (2005).
21. Chen, Y. & Webster, T. J. Increased osteoblast functions in the presence of BMP-7 short peptides for nanostructured biomaterial applications. J Biomed Mater Res A 91, 296-304, doi:10.1002/jbm.a.32246 (2009).
22. Caron, M. M. et al. Hypertrophic differentiation during chondrogenic differentiation of progenitor cells is stimulated by BMP-2 but suppressed by BMP-7. Osteoarthritis Cartilage 21, 604-613, doi:10.1016/j.joca.2013.01.009 (2013).
23. Caron, M. M. J. et al. BAPX1/NKX3.2 ACTS AS A CHONDROCYTE HYPERTROPHY MOLECULAR SWITCH IN OSTEOARTHRITIS. Arthritis & Rheumatology 67 (2015).
24. Gentilucci, L., De Marco, R. & Cerisoli, L. Chemical modifications designed to improve peptide stability: incorporation of non-natural amino acids, pseudo-peptide bonds, and cyclization. Curr Pharm Des 16, 3185-3203 (2010).
25. Blaney Davidson, E. N. et al. Osteoarthritis Cartilage 23, 478-486, (2015).
26. Glasson, S. S. et al. Nature 434, 644-648, (2005).
27. Takayama, K. et al. Arthritis Res Ther 16, 482, (2014).
28. Hayashi, et al. Arthritis Res Ther 10, R118, (2008).
29. Sekiya, I. et al. J Orthop Res 27, 1088-1092, (2009).
30. Pritzker, K. P. et al. Osteoarthritis Cartilage 14, 13-29, (2006).
31. Kirkwood, et al., J. Oral Implant. 24: 57-65 (2003)
32. Renner, J. et al., Tissue Engineering 18: 2581-2589 (2012).

The invention claimed is:

1. A method for the treatment or amelioration of osteoarthritis, the method comprising:
   administering to a subject in need thereof a therapeutically effective amount of a peptide;
   wherein the peptide consists of an amino acid sequence according to SEQ ID NO: 18 or an analogue thereof,
   wherein the analogue is a peptide consisting of an amino acid sequence according to formula 1 (SEQ ID NO: 29), or a fragment thereof;
   wherein the fragment consists of at least 10 consecutive amino acids of SEQ ID NO: 18 or an amino acid sequence according to formula 1,
   wherein formula 1 is:

(SEQ ID NO: 29)
   P K P S S X1 P X2 X3 L X4 X5 I X6 V X7 X8 X9 D X10 X11 X12 X13 X14 X15 X16 X17 X18 X19 X20 X21 M V V X22 X23 S G S X24, wherein;
   X1=A or V
   X2=T or D or E
   X3=Q or D or K or S
   X4=N or D or E or H
   X5=A or D or S
   X6=S or l or L or M or F or Y or E or H or K or Q or R or D
   X7=L or E or K or T or M or R
   X8=Y or A or D or E or H or K or S or T
   X9=F or H or A or D or E or K or Q or R or Y
   X10=D or l or L or E or N or S or T
   X11=S or D or E or N or R
   X12=S or D or E or K or N or T
   X13=N or E or Q or R
   X14=V or A or D or N or R or T or M or Y or H
   X15=I or A or D or E or K or N or Q or R or S or T or V
   X16=L or A or E or K or Q
   X17=K or D or E or G or Q or R or W
   X18=K or A or D or E or H or N or P or Q or S or T or I or V or M
   X19=Y or D or E or H or K or Q or I or R
   X20=R or D or E or K or N or S
   X21=N or D
   X22=R or E or S or D or K or Q or L
   X23=A or E or D or S
   X24=H or R; and
   wherein the fragment comprises Leu at a position corresponding to position 16 of SEQ ID NO: 29 or Ser at a position corresponding to position 37 of SEQ ID NO: 29.

2. The method according to claim 1, wherein the analogue of SEQ ID NO: 18 comprises 24, 23, 22, 21, 20, 19, 18, 17, 16, 15, 14, 13, 12, 11, 10, 9, 8, 7, 6, 5, 4, 3, 2 or 1 amino acid substitution(s) selected from the group consisting of substitutions X1, X2, X3, X4, X5, X6, X7, X8, X9, X10, X11, X12, X13, X14, X15, X16, X17, X18, X19, X29, X21, X22, X23, and X24.

3. The method according to claim 1, wherein the peptide is selected from the group consisting of linear peptides, cyclic peptides, mono-looped peptides, and two-looped peptides.

4. The method according to claim 1, wherein the treatment further comprises the administration of at least one polypeptide,
   wherein the polypeptide is between 12 and 28 amino acids in length and comprises an amino acid sequence according to SEQ ID NO: 30 or a variant thereof according to SEQ ID NO: 31, and
   wherein the amino acid sequence of the polypeptide is comprised in SEQ ID NO: 32 or a variant thereof according to SEQ ID NO: 33.

5. The method according to claim 4, wherein the variant according to SEQ ID NO: 33 comprises 12, 11, 10, 9, 8, 7, 6, 5, 4, 3, 2 or 1 amino acid substitution(s) selected from the group consisting of substitutions Z1, Z2, Z3, Z4, Z5, Z6, Z7, Z8, Z9, Z10, Z11, Z12 and Z13, wherein;
   Z1=A or I or L or M or Y or V or E or H or K or Q or R,
   Z2=P or Y or M,
   Z3=E or R or H or K or N or P or Q or S or T or I or L or M or V,
   Z4=A or E or Q or R or S,
   Z5=Y or N or D,
   Z6=E or A or Q,
   Z7=A or D or E or H or K or S,
   Z8=F or A or D or E or H or Q or R or S,
   Z9=P or M,
   Z10=N or A or D or S or T or E or Q or R or I or V,
   Z11=S or A or D or E or H or K or N or P or Q or T,
   Z12=Y or H or D or G or H or N or R or S or T or wherein
   Z13=N or F or W or Y or H or K or R.

6. The method according to claim 4, wherein the variant according to SEQ ID NO: 31 comprises 5, 4, 3, 2 or 1 amino acid substitution(s) selected from the group consisting of substitutions Z6, Z7, Z8, Z9, Z10 and Z11, wherein
   Z6=E or A or Q,
   Z7=A or D or E or H or K or S,
   Z8=F or A or D or E or H or Q or R or S,
   Z9=P or M,
   Z10=N or A or D or S or T or E or Q or R or I or V or wherein
   Z11=S or A or D or E or H or K or N or P or Q or T.

7. The method according to claim 4, wherein the polypeptide comprises an amino acid sequence according to SEQ ID NO: 30.

8. The method according to claim 4, wherein the amino acid sequence of the polypeptide is fully comprised in SEQ ID NO: 32.

9. The method according to any one of claims 4-8 wherein the polypeptide is selected from the group consisting of linear peptides, cyclic peptides, mono-looped peptides, and two-looped peptides.

10. The method according to claim 4, wherein the polypeptide consists of an amino acid sequence selected from the group consisting of SEQ ID NOs: 34-48 and SEQ ID NOs: 50-64.

* * * * *

UNITED STATES PATENT AND TRADEMARK OFFICE
CERTIFICATE OF CORRECTION

PATENT NO. : 10,639,352 B2
APPLICATION NO. : 16/092680
DATED : May 5, 2020
INVENTOR(S) : Tim Johannes Maria Welting and Marjolein Maria Johanna Caron It is certified that error appears in the above-identified patent and that said Letters Patent is hereby corrected as shown below:

In the Claims

In Column 46, Line 19, in Claim 2, please replace "X12, X13, X14, X15, X16, X17, X18, X19, X29, X21, X22," with -- X12, X13, X14, X15, X16, X17, X18, X19, X20, X21, X22, --

Signed and Sealed this
Eleventh Day of January, 2022

Drew Hirshfeld
*Performing the Functions and Duties of the
Under Secretary of Commerce for Intellectual Property and
Director of the United States Patent and Trademark Office*